(12) United States Patent
Robert

(10) Patent No.: US 9,950,086 B2
(45) Date of Patent: Apr. 24, 2018

(54) FIXTURE SANITIZER

(71) Applicant: Michael E. Robert, Farmington Hills, MI (US)

(72) Inventor: Michael E. Robert, Farmington Hills, MI (US)

(73) Assignee: DM TEC, LLC, Livonia, MI (US)

( * ) Notice: Subject to any disclaimer, the term of this patent is extended or adjusted under 35 U.S.C. 154(b) by 0 days.

(21) Appl. No.: 14/834,026

(22) Filed: Aug. 24, 2015

(65) Prior Publication Data

US 2016/0051713 A1    Feb. 25, 2016

Related U.S. Application Data

(63) Continuation-in-part of application No. PCT/US2015/020288, filed on Mar. 12, 2015.

(60) Provisional application No. 62/040,444, filed on Aug. 22, 2014, provisional application No. 61/952,007, filed on Mar. 12, 2014, provisional application No. 61/970,661, filed on Mar. 26, 2014, provisional application No. 62/115,373, filed on Feb. 12, 2015.

(51) Int. Cl.
*A61L 2/14* (2006.01)
*C02F 1/46* (2006.01)
*C02F 1/467* (2006.01)

(52) U.S. Cl.
CPC .............. *A61L 2/14* (2013.01); *C02F 1/4608* (2013.01); *C02F 1/4672* (2013.01); *C02F 2303/04* (2013.01)

(58) Field of Classification Search
USPC ........................................................ 361/231
See application file for complete search history.

(56) References Cited

U.S. PATENT DOCUMENTS

| | | | |
|---|---|---|---|
| 2,392,808 A | 1/1946 | Chapman |
| 2,928,941 A | 3/1960 | Hicks et al. |
| 3,443,155 A | 5/1969 | Schweriner |
| 3,584,766 A | 6/1971 | Hart |
| 3,609,446 A | 9/1971 | Hursh et al. |
| 3,697,806 A | 10/1972 | Herbert, Jr. |
| 3,816,793 A | 6/1974 | Radloff et al. |
| 3,828,239 A | 8/1974 | Nagai et al. |
| 3,840,797 A | 10/1974 | Aggen et al. |
| 3,866,086 A | 2/1975 | Miyoshi et al. |
| 3,878,469 A | 4/1975 | Bolasny |

(Continued)

FOREIGN PATENT DOCUMENTS

| | | |
|---|---|---|
| CN | 2169935 | 6/1994 |
| CN | 2235509 | 9/1996 |

(Continued)

OTHER PUBLICATIONS

Prutchi et al., "d.i.y. 250 kV High Voltage DC Power Supply with Neat Trick for Switching Polarity," http://www.diyphysics.com/2012/02/09/d-i-y-250-kv-high-voltage-dc-power-supply-with-neat-trick-for-switching-polarity/ (accessed May 8, 2015).

(Continued)

*Primary Examiner* — Scott Bauer
(74) *Attorney, Agent, or Firm* — Craig A. Phillips; Dickinson Wright PLLC

(57) ABSTRACT

A sanitizer for sanitizing various plumbing fixtures and specifically, to a chemical-free sanitizer, more specifically to an ozone-free sanitizer, and yet more specifically to an electronic sanitizer using ions.

26 Claims, 21 Drawing Sheets

(56) References Cited

U.S. PATENT DOCUMENTS

| | | | |
|---|---|---|---|
| 3,943,407 A | 3/1976 | Bolasny | |
| 3,981,695 A | 9/1976 | Fuchs | |
| 4,069,665 A | 1/1978 | Bolasny | |
| 4,282,460 A | 8/1981 | Luz et al. | |
| 4,292,592 A | 9/1981 | Birdwell et al. | |
| 4,301,497 A | 11/1981 | Johari | |
| 4,597,781 A | 7/1986 | Spector | |
| 4,616,300 A | 10/1986 | Santelmann, Jr. | |
| 4,689,715 A | 8/1987 | Halleck | |
| 4,789,801 A | 12/1988 | Lee | |
| 4,893,227 A | 1/1990 | Gallios et al. | |
| 4,974,115 A | 11/1990 | Breidegam et al. | |
| 5,010,869 A | 4/1991 | Lee | |
| 5,055,963 A | 10/1991 | Partridge | |
| 5,057,966 A * | 10/1991 | Sakata | H05F 3/04 361/213 |
| 5,065,272 A * | 11/1991 | Owen | A61N 1/44 361/231 |
| 5,317,155 A | 5/1994 | King | |
| 5,452,720 A | 9/1995 | Smith et al. | |
| 5,484,472 A | 1/1996 | Weinberg | |
| 5,930,105 A | 7/1999 | Pitel et al. | |
| 6,042,637 A * | 3/2000 | Weinberg | A61L 9/22 361/235 |
| 6,201,359 B1 | 3/2001 | Raets | |
| 6,771,519 B2 | 8/2004 | Frus et al. | |
| 7,218,500 B2 | 5/2007 | Adachi | |
| 7,564,671 B2 | 7/2009 | Kato et al. | |
| 7,601,970 B2 | 10/2009 | Lee | |
| 7,649,728 B2 | 1/2010 | Fujita et al. | |
| 7,662,348 B2 | 2/2010 | Taylor et al. | |
| 7,854,900 B2 | 12/2010 | Takeda et al. | |
| 7,920,368 B2 | 4/2011 | Fujiwara et al. | |
| 7,995,321 B2 | 8/2011 | Shimada | |
| 8,009,405 B2 | 8/2011 | Gefter et al. | |
| 8,149,371 B2 | 4/2012 | Oohira et al. | |
| 8,605,407 B2 | 12/2013 | Gefter et al. | |
| 8,773,837 B2 | 7/2014 | Partridge et al. | |
| 8,885,317 B2 | 11/2014 | Partridge | |
| 2002/0014410 A1 | 2/2002 | Silveri et al. | |
| 2004/0184975 A1 | 9/2004 | Anno | |
| 2005/0028254 A1 | 2/2005 | Whiting | |
| 2006/0018811 A1 | 1/2006 | Taylor et al. | |
| 2006/0243762 A1 | 11/2006 | Sassoon | |
| 2007/0279829 A1 | 12/2007 | Gefter et al. | |
| 2008/0250928 A1 | 10/2008 | Desalvo et al. | |
| 2009/0316445 A1 | 12/2009 | Mowrer et al. | |
| 2010/0064545 A1 | 3/2010 | Pollack et al. | |
| 2010/0065535 A1 | 3/2010 | Zheng et al. | |
| 2010/0157503 A1 | 6/2010 | Saito et al. | |
| 2011/0102963 A1 | 5/2011 | Sekoguchi | |
| 2011/0133098 A1 | 6/2011 | Kitagaito et al. | |
| 2011/0150710 A1 | 6/2011 | Tsuda et al. | |
| 2012/0081929 A1 | 4/2012 | Dvorsky | |
| 2012/0200982 A1 | 8/2012 | Partridge | |
| 2012/0224293 A1 | 9/2012 | Partridge et al. | |
| 2012/0240968 A1 | 9/2012 | Schumacher | |
| 2012/0314333 A1 | 12/2012 | Takeda et al. | |
| 2013/0095000 A1 | 4/2013 | Yamamoto et al. | |
| 2013/0201730 A1 | 8/2013 | Luo | |
| 2013/0232807 A1 | 9/2013 | Robert et al. | |
| 2014/0285084 A1 | 9/2014 | Fomani et al. | |
| 2016/0104595 A1 | 4/2016 | Nishida et al. | |

FOREIGN PATENT DOCUMENTS

| | | | |
|---|---|---|---|
| CN | 1536281 | | 10/2004 |
| CN | 201311011 | | 9/2009 |
| CN | 203423631 | | 2/2014 |
| CN | 203481626 | | 3/2014 |
| EP | 0368858 | | 5/1995 |
| EP | 1637811 | | 3/2006 |
| EP | 1625890 | | 6/2011 |
| JP | 2001043992 | | 2/2001 |
| JP | 2002216994 | | 8/2002 |
| JP | 5185250 | | 4/2013 |
| KR | 20020090178 A | * | 11/2002 |
| WO | 2010144528 | | 12/2010 |
| WO | 2013119283 | | 8/2013 |

OTHER PUBLICATIONS

"Flyback Transformer," Wikipedia, http://en.wikipedia.org/wiki/Flyback_transformer (accessed May 8, 2015).

"Basic Single-Output Flyback Converter Circuit Diagram," http://datasheetoo.com (accessed May 14, 2014).

Schmidt et al., "Microfabricated differential mobility spectrometry with pyrolysis gas chromatography for chemical characterization of bacteria," Anal Chem. 2004, Abstract.

International Search Report, dated Jun. 25, 2015 (PCT/US2015/020288).

Gadri, Ben et al.; Sterilization and plasma processing of room temperature surfaces with a one atmosphere uniform glow discharge plasma (OAUGDP); Surface & Coatings Technology; vol. 131, pp. 528-542 (2000).

\* cited by examiner

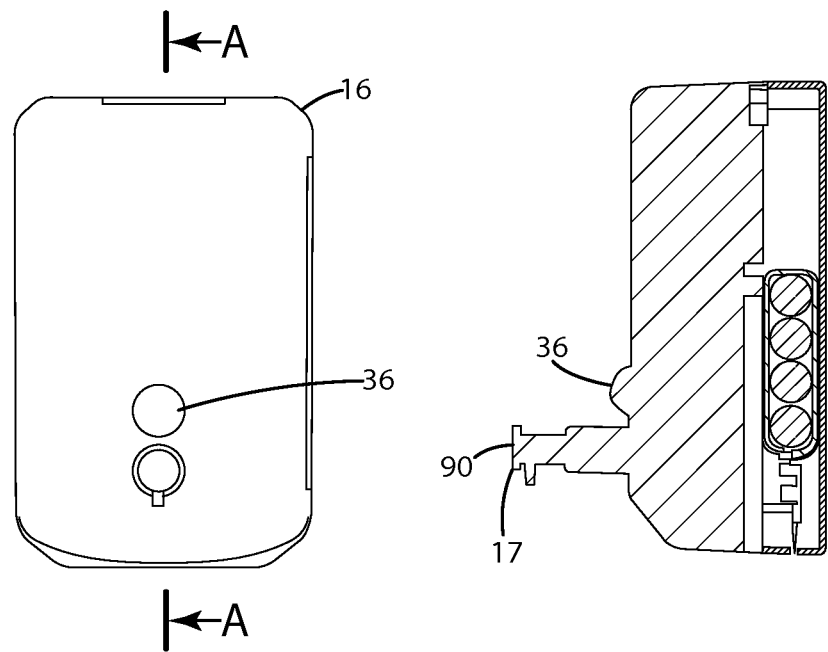
Fig. 18
Fig. 19
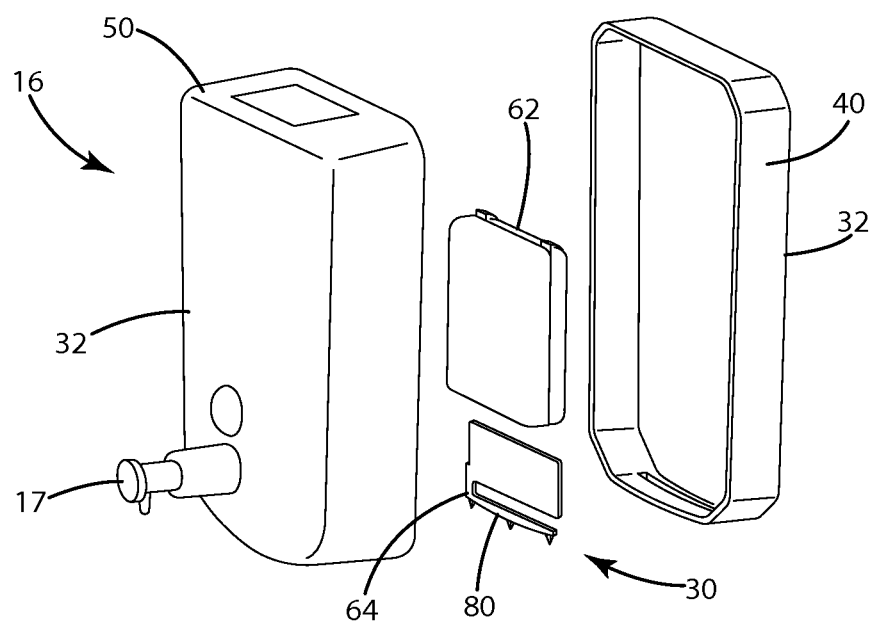
Fig. 20

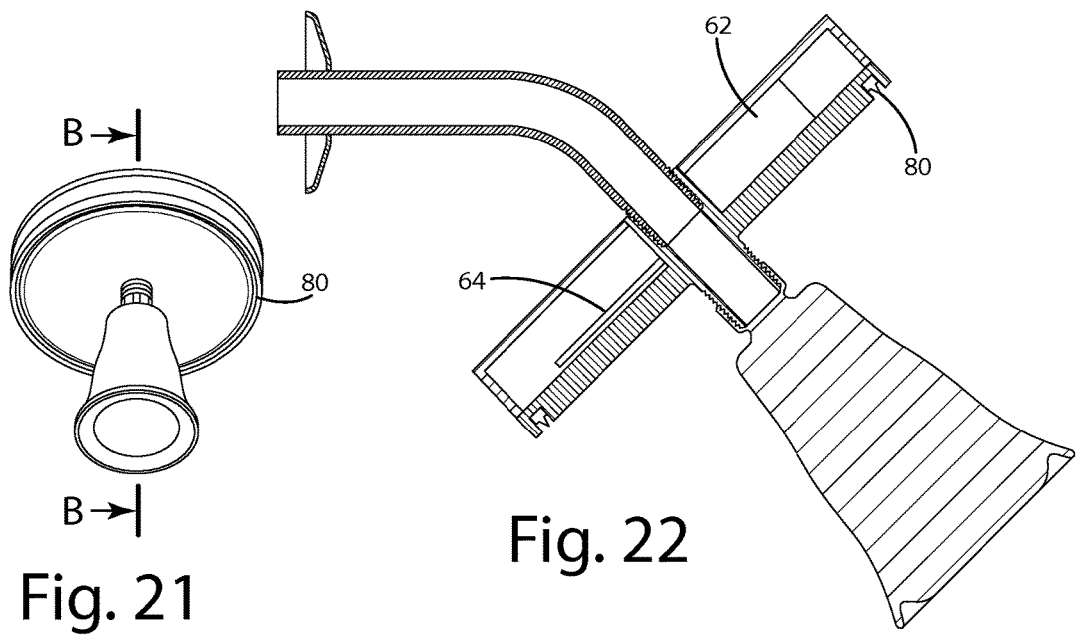
Fig. 21
Fig. 22
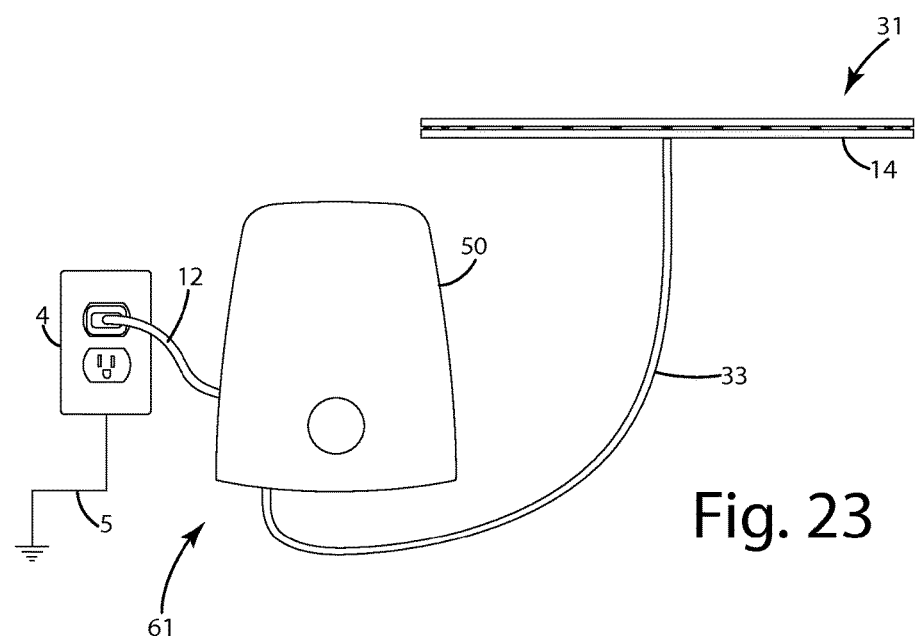
Fig. 23

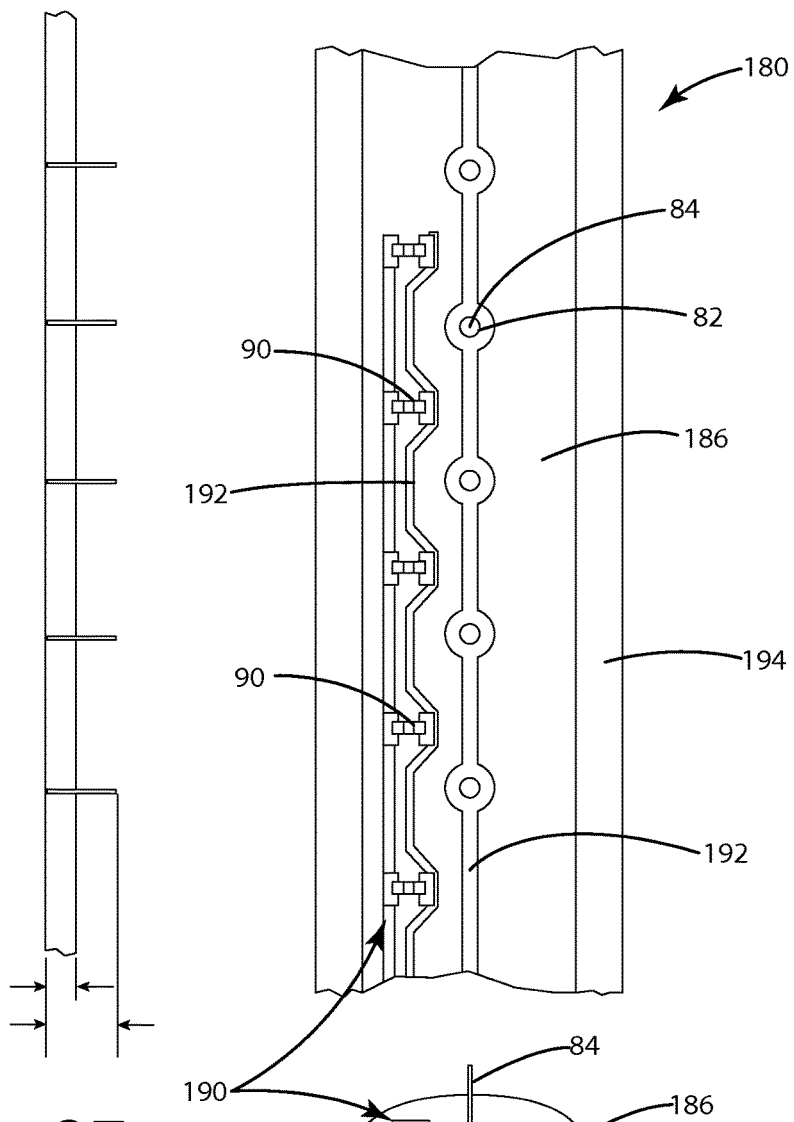
Fig. 27
Fig. 28
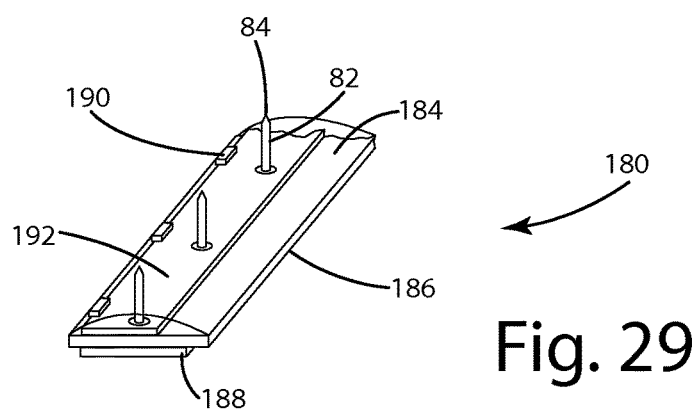
Fig. 29

HIGH VOLTAGE AC GENERATOR

HVAC OUTPUT

EXAMPLE FLYBACK CONVERTER CIRCUIT USED TO CREATE
HIGH VOLTAGE DC FOR BIPOLAR IONIZATION.

EXAMPLE OUTPUT OF FLYBACK CONVERTER WITH 5V SQUARE
WAVE INPUT AND 1.25KV PEAK DC OUTPUT

EXAMPLE OF FLYBACK CONVERTER USING PRIMARY FEEDBACK TO RESONATE

VOLTAGE MULTIPLIER CIRCUIT. CAN BE REPEATED FOR V_OUT= X VIN

STEP UP TRANSFORMER METHOD OF HIGH VOLTAGE AC SUPPLY

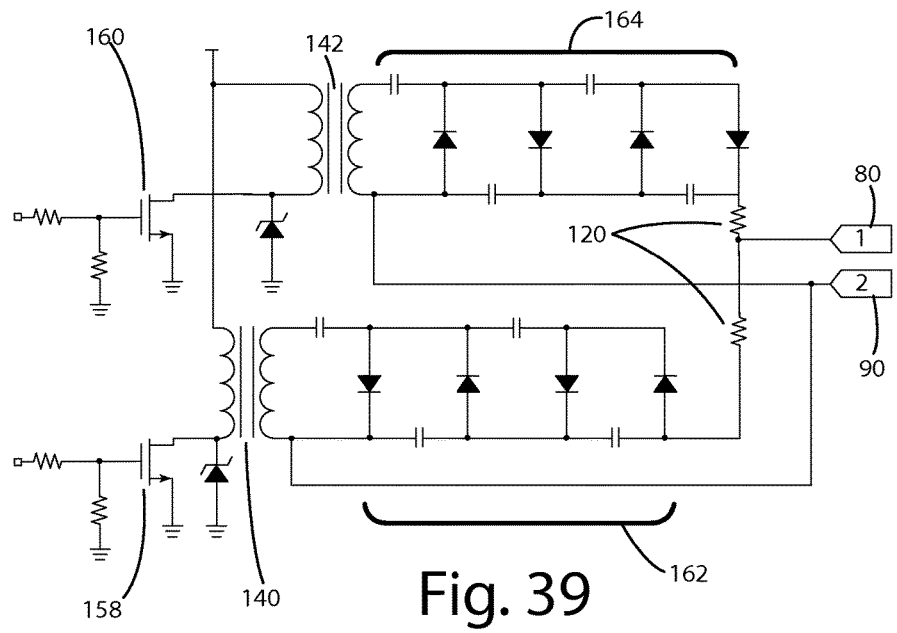
Fig. 39
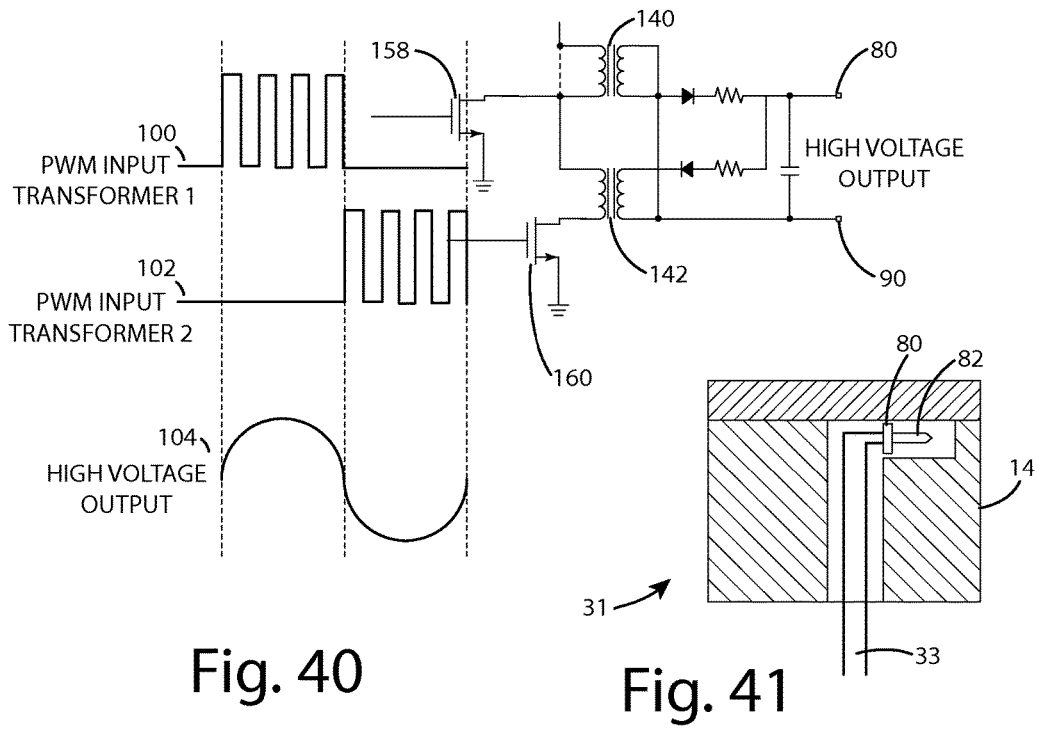
Fig. 40
Fig. 41

FIXTURE SANITIZER

CROSS-REFERENCE TO PRIOR APPLICATION

This application is a Continuation-In-Part of PCT Patent Application International Serial No. PCT/US2015/020288 filed Mar. 12, 2015 entitled "Sanitizer," which claims the benefit of and priority to U.S. Provisional Patent Application Ser. No. 61/952,007 filed Mar. 12, 2014 entitled "Sanitizer," U.S. Provisional Patent Application Ser. No. 61/970,661 filed Mar. 26, 2014 entitled "Ion Generator," and U.S. Provisional Patent Application Ser. No. 62/115,373 filed Feb. 12, 2015 entitled "Ion Generator", and claims the benefit of U.S. Provisional Patent Application Ser. No. 62/040,444 filed Aug. 22, 2014, entitled "Fixture Sanitizer," the entire disclosure of the application being considered part of the disclosure of this application and hereby incorporated by reference.

BACKGROUND OF THE INVENTION

1. Field of the Invention

The present invention is directed to a sanitizer for sanitizing various fixtures and appliances, such as faucets, handles and other items touched by humans and more specifically, to a chemical-free sanitizer, more specifically to an ozone-free sanitizer, and yet more specifically to an electronic sanitizer producing ions to sanitize surfaces.

2. Description of the Prior Art

It is well known that many infectious diseases and pathogens are communicated through touch or contact. Therefore, commonly touched items in public areas and facilities such as doorknobs, handles, fixtures, and other surfaces may spread infectious diseases and pathogens. People are particularly concerned with touching various surfaces in public restrooms, even communal restrooms at a work place or otherwise due to actual or perceived sanitary conditions of those restrooms and the users of the restrooms. In addition, many kitchens, both commercial and at-home, during food preparation may come in contact with various infectious diseases and pathogens, whether attributable to people, the food preparation or other sources. Many infectious diseases and pathogens may be transferred by various plumbing fixtures such as faucet handles and appliances, such as handles and controls, during normal use of a kitchen. As such, while contact with door handles, knobs and other plumbing fixtures related to the restroom and kitchen at many times is desirable to avoid for the above reasons, such contact is generally unavoidable and the transfer of infectious diseases from those surfaces to a person or from a person to those surfaces is also unavoidable. As such, many surfaces may be contaminated with pathogens and infectious diseases from people or other sources. Therefore, most people generally find it desirable to avoid or minimize contact with such surfaces when possible.

People are particularly concerned with the cleanliness of surfaces after washing their hands or before eating of food. However, touching many of the surfaces in a kitchen or a restroom after washing the hands or while preparing food at home, in work place kitchens, and in commercial kitchens is unavoidable. For example, in most kitchens, whether at home, at work, or in a commercial setting, such as a restaurant, the person must touch the handle of the faucet to turn on or off the water. As the person turns on the water, they may contaminate the faucet handle with a pathogen and after washing their hands, when turning off the water, they could potentially contact a surface that they just contaminated or was previously contaminated. As such, it is very easy to recontaminate a person's hands, even after being properly washed. In a kitchen, other than door and fixture handles, such as faucets, a refrigerator door handle, and kitchen knobs, the surface of a microwave, and the touch surfaces of many other appliances, including switches, knobs and other controls and even further, lighting switches, may all be contaminated with various pathogens and infectious diseases.

Some people use extra paper towels to cover and touch handles of a door or faucet handles; however, generally this is wasteful and adds additional expense for a facility, including increased paper cost as well as increased labor cost for replacing the paper products more frequently. In addition, in the home environment, people rarely take these steps that they would in a public area, even though the surface may be just as contaminated, particularly during certain food preparation tasks.

A number of methods have been proposed or are commonly followed, all of which have limited success or significant drawbacks in sanitizing and maintaining the cleanliness of various surfaces, including faucet handles. The first method is generally a more frequent cleaning of such surfaces; however, this increases labor costs and generally people are distrustful in public settings that the surfaces have been properly cleaned with enough frequency. Even in home settings, people may not realize just how contaminated their hands or a particular surface is at any given time. In addition, even if the fixture or surface was cleaned properly and no pathogens exist on the surface after cleaning, the very first contact by a person may place an undesirable infectious agent or pathogen on such surface or fixture and any subsequent users, or even the same user may later come in contact with such infectious agents or pathogens. For example, a person preparing chicken may encounter salmonella bacteria. The *salmonella* bacteria may be on their hands such that when they turn on the faucet, they contaminate the handle of the faucet before cleaning their hands. After turning on the faucet, they wash their hands, but when turning off the faucet, they recontaminate their hands by touching the surface of the handle to the faucet. Even a soap dispenser or soap bottle may be the contaminated item.

A number of other sanitizing methods have been proposed, all having limited success or significant drawbacks in sanitizing various surfaces. Most sanitizers have been directed to door handles and restroom fixtures other than sink faucets and soap dispensers. Today, no device exists that sanitizes on an automatic basis the handles of a faucet or likewise, a soap dispenser. One prior method of addressing sanitization of surfaces and fixtures is generally a more frequent cleaning of such surfaces; however, this increases labor costs and generally people are distrustful, rightfully so that the surfaces have been properly cleaned with enough frequency. As stated above, a surface may be contaminated with one touch by a person having the pathogen or infectious disease on their hands and, as such, may self-contaminate themselves. Therefore, even if the best and most thorough cleaning process is completed with a substantial regular frequency, the surfaces may have infectious agents or pathogens from the very first contact of a person and any subsequent person or the even the same user may be contaminated with such infectious agents or pathogens after touching the surface or fixture. Therefore, more frequent cleanings do not generally solve the problem of contaminated surfaces and fixtures.

Some facilities provide various cleaning wipes, liquids, or sponges that may be used for cleaning the surface by a user such as ready-wipes or alcohol cleaners that are one time use. The big disadvantage to these wipes, liquids or sponges is that they require frequent replacement thereby increasing the cost for the facility, both in material costs and labor costs. Many times, anti-bacterial sprays, liquids or wipes are empty creating an undesirable situation for the person using a facility.

To address the above problems, some manufacturers have introduced various electronic chemical sanitizers that at regular intervals with little to no interaction with the user or upon activation of a sensor, spray liquid on the desired surface. In addition to the increased maintenance cost as well as the product cost of replacing batteries and chemicals or wet materials in these chemical sanitizers, most people find it undesirable to touch a moist or damp surface such as a moist or damp faucet handle or door handle even if the moisture or liquid is a sanitizing chemical. Furthermore, in a kitchen setting, many of these sanitizers or cleaners are undesirable near food preparation areas, particularly when they have automatic releases which may occur when food is in close proximity. As such, traditionally these sanitizers using chemicals or the like have occurred only in restroom facilities and have been used even then in limited circumstances, typically without any plumbing fixtures. In addition, many people do not like the smell or have various chemical allergies to the chemicals being used to sanitize the surface such as a door handle or other fixture. More specifically, such as in an office setting, if one worker has a chemical allergy to the cleaning device that is being used, which on a timed or activated interval sprays a fixture such as a door handle, it may prevent that user from using the facility or even in some circumstances prevents use of the device in that facility.

To address some of the above problems with chemical sanitizers, some people have proposed using ultraviolet sanitizers that when positioned or placed over a non-porous surface effectively sterilizes and sanitizes the surface. While such devices prevent the spread of pathogens passed on by contact or direct exposure by exposing the pathogens to a killing ultraviolet light, these devices generally are power intensive and require frequent battery changes or recharging, unless they are hardwired into a facility's electrical system, which is expensive. Also, these ultraviolet light sanitizers if not properly positioned or configured may have adverse health effects and to date, none have been capable of sanitizing fixtures such as faucet handles, soap dispensers and related surfaces without potentially exposing the user to ultraviolet light. Repeated, frequent exposure to ultraviolet light from these devices is typically undesirable and may have adverse health effects. Therefore, to sanitize faucets, soap dispensers and the like, which do not typically have readily available power supplies, even where there is use of a controlled or preprogrammed timer or even motion sensor to limit battery drain, the use life is relatively limited requiring regular maintenance to replace or recharge batteries. Many people are also concerned with placing their hands on a door handle, faucet handle, soap dispenser or other fixture or appliance where it may be bathed in ultraviolet light. The positioning of many of these ultraviolet devices are typically above a door handle or counter top, which places it high enough such that children and smaller people may inadvertently look directly at the ultraviolet lamp, is undesirable and could cause in certain circumstances especially after repeated exposure, vision issues. Therefore, the implementation of these devices as sanitizers for various fixtures that cannot fit in an enclosure has been limited due to their serious drawbacks.

To address the shortcomings with various chemical and ultraviolet light sanitizers, some manufacturers have introduced ozone sanitizers, which is known to be a potent sanitizer for killing various pathogens as it is a highly reactive oxidizer. Ozone works well at killing various pathogens without leaving any chemical residue on the treated surface and therefore, has been highly desirable for use in food processing plants, but otherwise has had limited practical applications. A sanitizing processing system using ozone is generally of limited use because the system must control the output of ozone in a sealed environment due to various potential health issues related to exposure to ozone. Therefore, even though ozone was used as a sanitizer more widely before its health effects were known, it is now limited to large industrial settings and has not been successfully implemented currently in households or small commercial applications. More specifically, the application of ozone sanitizing systems has been extremely limited by the more recent understanding that ozone may cause various health issues, including according to the EPA, respiratory issues such as lung function, decrements, inflammation and permeability, susceptibility to infection, cardiac issues and increasing respiratory symptoms including increased medication use, asthma attacks and more. Exemplary respiratory systems from ozone exposure can include coughing, throat irritation, pain, burning, or discomfort in the chest when taking a deep breath, chest tightness, wheezing or shortness of breath. For some people, more acute or symptomatic responses may occur. As the concentration at which ozone effects are first observed depends mainly on the sensitivity of the individual, for some people even parts per billion exposure may cause noticeable issues. Therefore, other than in commercial environments where the ozone application must be specifically controlled, these systems are not desirable for a broader implementation in homes, work places and other facilities, where the ozone is not easily contained, such as any type of ozone sanitizer that would function as a fixture or a surface sanitizer. Therefore, there is a need for an effective sanitizer that does not include the identified limitations.

Existing sanitizers or ozone devices require a method of propelling the ions or ozone away from the device. As such, many of these devices use fans, compressed air, or other mechanisms for dispersing the ions. One problem with such systems is that in applications where an external power source is not readily available, batteries for fans, and other means of propulsion such as $CO_2$ canisters must be replaced on a fairly regular basis. In mechanisms using a fan powered by battery, the fans substantially limits the life of the battery to the point where it needs to be replaced weekly or even bi-weekly in certain environments. Other systems using compressed air or $CO_2$ require replacement or recharging of the cartridges or tanks on a regular basis. In addition, any sanitizer requiring a mechanism for propelling the ions outward such as the battery-powered fans or compressed air stop efficiently functioning, without the mechanism for propulsion.

Bipolar ionizers use a high voltage to create an electric field across two discharge points. One point creates positive ions and the other point creates negative ions. It is well known that as the number of points increases, the amount of ions that may be generated due to the nature of electrical fields and increase in surface area from using multiple points, is reduced. More specifically, the use of a single point requires that all of the electrical fields will pass through that point. As such, the production of ions is maximized by use of a single point. Traditionally, multiple points as ion sources were discouraged to maximize ion production. In addition, Bipolar ionizers use a high voltage to create an electric field across two discharge points. One point creates positive ions and the other point creates negative ions. (Note, multiple discharge points for positive and multiple discharge points for negative are acceptable). The most common methods of creating the required voltage are either a flyback transformer or a voltage multiplier circuit or a combination of the two, as illustrated in FIG. 34. These circuits are well known. Because the high voltage output is direct current (DC), two discharge points are required—one for positive and the other for negative. Most implementations of a flyback transformer use feedback from a secondary winding on the transformer to create a resonator that switches the primary side of the transformer on and off. While this circuit is simple and cost effective, it often takes long periods of time for the circuit to stabilize and reach its full output, as illustrated in the graph in FIG. 33, which shows just a small portion of the output at the peak, thereby limiting generation of ions.

In addition, certain pathogens are becoming resistant to various chemicals used in chemical sanitizers. For example, in the medical field, one of the biggest problems facing hospitals and clinics is pathogens that are resistant to various chemicals.

A number of ion generators also require thermal plasma to function. Thermals plasma ion generators produce ions, but are extremely hot, limiting their effective use in close proximity to humans, such as use in a hand sanitizer. As with any ions created by an ion generator, many of the ions are unstable and quickly convert back, limiting the effective range of the ions that are useful in sanitizing surfaces, including hands of various pathogens, yet it is desirable to space hands well away from any thermal plasma field. Therefore, thermal plasma devices have serious design constraints when used to sanitize surfaces, such as door handles and other fixtures that are in regular human contact, and any sanitizing of human body surfaces, such as hands in thermal plasma is not advisable and should be avoided. In addition, as stated above, many ion generators operate in a similar manner to ozone generators. Therefore, thermal plasma is generally undesirable because it may cause corona discharge, which is related to ozone production.

Another drawback to ion generators that use a thermal plasma is the high power consumption required to generate the thermal plasma. In general, any thermal plasma ion generator must be used connected to the power grid. Battery life of a thermal ion generator would be so short or require such large capacity batteries, therefore requiring large volumes of space, any use of the ion generator remote from the power grid would be impractical, and the maintenance requirements would be extremely high in relation to replacing or recharging the batteries. Therefore, ion generators that use thermal plasma are generally not useful to attach to doors, walls or other locations where it is difficult to connect them to the power grid. In addition, even if a thermal plasma ion generator may be placed in a position to connect to the power grid, the installation cost is typically high, and the high power consumption is expensive.

Most ion generators only generate a single type of ion, typically only negative ions. Any ion device only generating a single type of ion or more specifically, a single type of charge for the ions are generally not as effective as ion generators producing both positive and negative ions in killing pathogens to sanitize surfaces. Therefore, a need exists for an ion generator that is bipolar, not just monopolar, and more specifically, an ion generator that produces sufficient quantities of positive and negative ions.

Some sanitizers require expensive sacrificial anodes or cathodes. Sacrificial anodes or cathodes must be replaced, and in addition, sacrificial anodes or cathodes put pieces of the anode or cathode in the environment, typically as ions in a fluid, which may subject the ion generator to numerous additional regulations. In addition, if either the cathodes, anode or fluid is depleted, the sanitizer ceases to function as desired.

SUMMARY OF THE INVENTION

The present invention is directed to a sanitizer for sanitizing various surfaces including hands, hardware, fixtures, appliances, countertops, equipment, utensils and more and more specifically to an ozone-free sanitizer and yet more specifically to an electronic sanitizer using alternating current (AC), not direct current (DC) voltage at the ion sources with a single ion electrode and a ground electrode, and a sanitizer that uses liquid, such as water to enhance the sanitizing effect of the plasma field, and more specifically, to a bipolar ion generator, capable of generating both positive and negative ions.

The present invention is directed to a sanitizer including an ion source assembly having a base and an ion electrode situated within the base, the ion electrode including at least one ion source; and an ion generator assembly having a controller within a housing and wherein the controller is in electrical communication with the ion electrode through a cable. The ion generator assembly may include a ground electrode or the controller may be in communication with an external power supply, wherein the controller is in communication with the a ground reference in the external power supply and specifically the controller is configured to use the external ground reference as a ground electrode. In addition, the controller may alternate the charge on the ion electrode. Furthermore, the fixture being sanitized, if conductive, may act as the ground electrode and be in electrical communication with the controller.

The base of the ion assembly has an external surface and wherein the ion electrode is behind the external surface, either in a groove recessed from the external surface, but visible and open to the surrounding environment, or set within a cavity and substantially sealed from or not visible from the surrounding environment. More specifically the ion electrode may be located in an internal cavity on the base. As such, the base itself through the use of the cavity may create the desired air gap between the points and adjacent surfaces, or the ion electrode may still have covers or domes over the points, even though it is within the cavity. Where the ion electrode is situated within a groove on the base, an ion point on the ion source does not extend out of the groove, past the external surface, primarily for protection of the users from the points.

The ion generator and ion electrodes are specifically configured to produce a non-thermal plasma field, as thermal plasma field would be very undesirable and produce ozone. The base of the ion source assembly, particularly the ion electrode, may situated proximate to a fixture, such as a faucet, and wherein the non-thermal plasma field may be tuned such that any water exiting the faucet must pass through the plasma field and wherein the water passing through the non-thermal plasma field produces ions in the water. Ions in the water may form all types of sanitizing chemicals including various peroxides.

The ion electrode may be formed from a flexible material with the ion sources protruding therefrom. For example, the ion electrode may be formed from a flexible conductive material, such as LED tape. In addition, LEDs may be incorporated with the ion sources, providing lighting arrangements while also sanitizing. The flexible material may include a conductive metal tape and a strip substrate over the conductive metal tape, and the ion sources are spaced apart from one another. A plurality of covers, domes or other shapes may be used to form an air gap over the ion sources, particularly the points to seal them from the surrounding environment. This prevents corrosion of the ion sources, prevents dust and dirt reducing the efficiency of the ion sources, and since the ion sources include a point, which may be sharp, the covers protect users from contacting the points.

The sanitizer may include a battery in electrical communication with the controller. A ground electrode may extend from the controller of be formed as part of the ion source assembly. In most instances, it has been found that the ion source assembly and the ion generation assembly can be located at least twelve inches apart. As such, the fixture sanitizer is good at sanitizing various fixtures, appliances, hardware and surfaces while remaining substantially unobtrusive, with only the ion electrode needing to be built into the appliance, fixture or proximate thereto. The base of the ion source assembly is optional and is configured to protection the ion sources.

The present invention is further directed to a fixture sanitizer for sanitizing fixtures, appliances, hardware and surfaces. The sanitizer includes an ion source assembly having an ion electrode, and if included a base in which the ion electrode is situated. The ion electrode includes at least one ion source. The sanitizer further includes an ion generator assembly having a controller configured to provide an AC output to the ion electrode. The controller is in electrical communication with the ion electrode and wherein the ion generator assembly is configured to receive electrical power from an external power supply having a reference ground and wherein the controller is configured to use the reference ground as a ground electrode. The ion electrode may be situated in a cavity on the base or the fixture and not visible or accessible from the external surface. In fact, the cavity may be sealed from the external surface. The base if it includes a sealed cavity, may include includes an inner surface and a passage extends between the inner surface and the cavity.

The present invention is further directed to a fixture sanitizer comprising an ion source assembly having an ion electrode including at least one ion source and wherein the ion electrode is formed from a flexible substrate to which the at least one ion source is coupled and a substrate cover configured to create an air gap around the ion source; and an ion generator assembly comprising a controller configured to provide an AC output to the ion electrode and wherein the controller is in electrical communication with the ion electrode and wherein the ion generator assembly is configured to receive electrical power from an external power supply having a reference ground and wherein the controller is configured to use the reference ground as a ground electrode. The substrate cover may seal the ion source from the surrounding environment, yet the air gap prevents the ion source from touching the substrate cover proximate to a point on the ion source.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 18 front elevational view of a soap dispenser including the sanitizer of the present invention;

FIG. 19 is a cross sectional view of the soap dispenser taken along lines A-A in FIG. 18;

FIG. 20 is an exploded right side perspective view of the soap dispenser of FIG. 18;

FIG. 21 is a front view of the sanitizer on a shower head as the fixture;

FIG. 22 is a partial cross-sectional view along lines B-B in FIG. 39;

FIG. 23 is a front elevational view of the sanitizer in FIG. 7;

FIG. 27 is a size view of an exemplary flexible ion electrode, including ion sources;

FIG. 28 is a top view of an exemplary flexible ion electrode, including ion sources and LEDs.

FIG. 29 is a top perspective view of a portion of a flexible ion electrode, including LEDs and emitters;

FIG. 39 is a partial schematic diagram of an exemplary ion generator;

FIG. 40 is a schematic diagram of a simplified version of the ion generator;

FIG. 41 is a cross sectional view of the ion source assembly in FIG. 26 along lines C-C;

DETAILED DESCRIPTION

Figure 1:
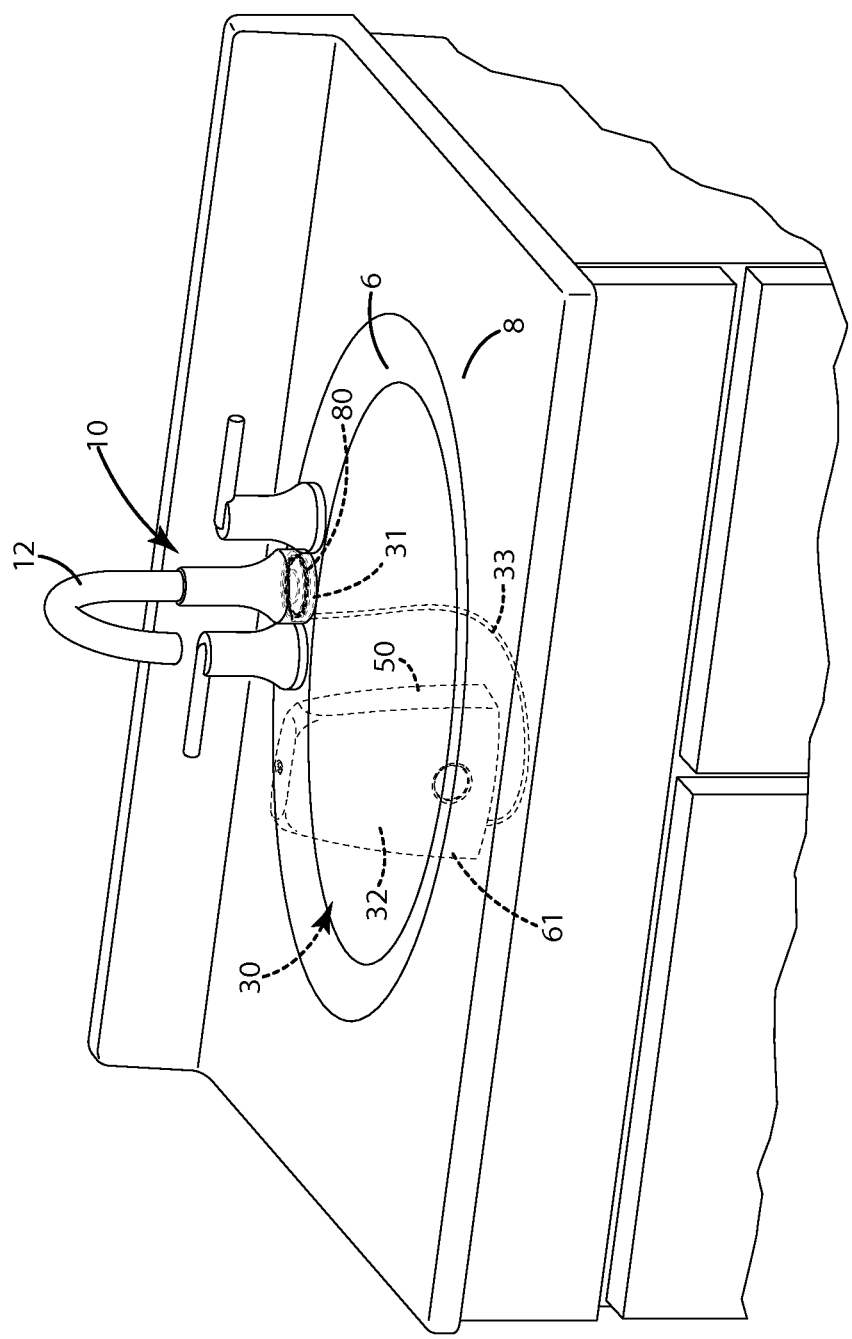
FIG. 1 is perspective view of the sanitizer with the ion generator assembly being located in a sink cabinet, and the ion source assembly forming the base of the faucet.
Figure 2:
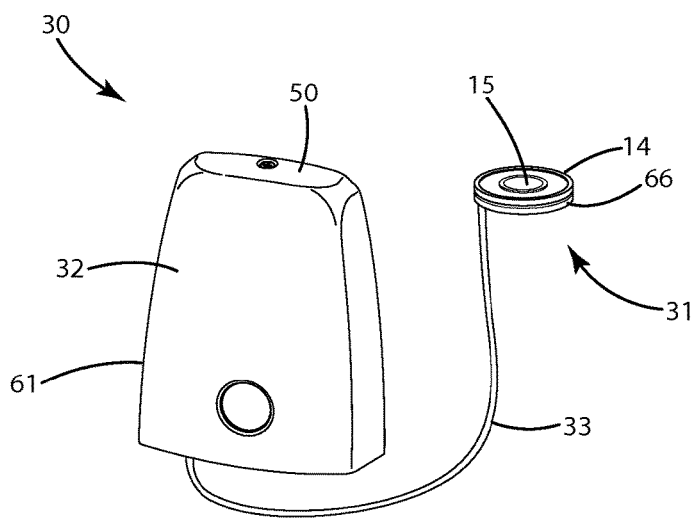
FIG. 2 is a top front perspective view of an exemplary sanitizer configured for use with a single faucet, soap dispenser, handle, or other fixture.

The present invention is generally directed to a sanitizer 30 for sanitizing various surfaces including hands. The ion generator 60 for the sanitizer 30 as described below generally produces charged ions that are expelled by the sanitizer 30 toward an object or surface to be sanitized using the electrical field of the ion generator 60. The ion generator 60 is specifically configured to avoid the production of ozone and should not be confused with ozone sanitizers. Instead, the present invention provides a compact sanitizer 30 that generates ions while avoiding the production of ozone during normal operation and therefore sanitizes surfaces without any ozone. Careful configuration of the ion sources and voltage is required to avoid the production of ozone.

Bipolar ionization of a gas creates plasma that is not in thermodynamic equilibrium because the ion temperature is lower than the electron temperature. This plasma is commonly referred to as 'cold plasma' or 'non-thermal plasma' because it occurs at room temperatures. Plasmas in thermodynamic equilibrium require much more energy and occur at significantly higher temperatures. Cold plasma has many benefits that will be discussed in greater detail. These benefits include, but are not limited to the ability to kill harmful pathogens including bacteria, mycoplasma, viruses, and mold. Additionally, cold plasma may help with a reduction of Volatile Organic Compounds (VOC's) and a reduction of particulates in the air including known allergens. Furthermore, cold plasma also reduces or eliminates static electricity in the air.

An ion is a molecule that is either positively or negatively charged. Most ions are unstable. A negative ion has at least one extra electron to give up in order to become stable. A positive ion is missing at least one electron that it must gain to become stable. It is believed that such instability of ions creates the desired electrochemistry capable of killing harmful pathogens including, but not limited to bacteria, mycoplasma, viruses, and mold.

Ions created in the air are referred to as 'air ions' or sometimes, simply 'ions'. Air ions may be classified by their charge and mobility. An air ion will move in the presence of an electric field due to its charge. The velocity of the air ion is proportional to the strength and direction of the electric field given in Volts per meter (V/m). With velocity given in m/s:

Mobility, $\mu=(m/s)/(V/m)=m2/Vs$

Where; m=distance in meters, s=time in seconds, and V=electrical potential in Volts.

The drift velocity (Vd) of an air ion is proportional to the Electric Field and inversely proportional to its mass. Therefore, smaller ions in a large electric field will have the greatest drift velocity.

Examples of air ions include small stable negative ions such as an Oxide molecule ion (O2−+(H2O)n), Carbon dioxide ion (CO3−+(H2O)n), and Nitric acid ion (NO3−+(H2O)n). Other examples of air ions include small stable positive ions such as a Hydrogen ion (H++(H2O)n), and Oxonium ion (H3O++(H2O)n). Additional examples of air ions include radicals such as Hydroxyl Radical (OH•).

The inventors have found that needle points, surprisingly, a plurality of them is the most simple, cost effective and energy efficient method of bipolar ionization. A high voltage AC or DC source is applied to needles, which are a non-grounded conductive surface, causing them to build up a positive or negative change on that surface. If the surface has a sharp tip with near-zero surface area there will not be enough surface to hold the charge and the energy of the charge will be dissipated into the surrounding air to create ions.

The sanitizer 30, as illustrated in the Figures, generally includes an ion generation assembly 61 and a source assembly 31 interconnected such as being electrically connected with the illustrated cord 33. The sanitizer 30, as illustrated in the Figures, allows the source assembly 31 to be placed remotely from the ion generation assembly 61. Therefore, a variety of functional uses may be provided that previously were not available when the ion generation assembly 61 and the source assembly 31 were housed as a single unit. As illustrated in the Figures, the sanitizer 30 generally includes the ion generation assembly 61 that includes an ion generator 60 having a controller 64 and is generally fit within a housing 32 having a cover 50 and a back plate or base 40. The housing 32 is generally meant to protect the interior components and provide a pleasing look and feel to the sanitizer and allow easy mounting to a variety of surfaces. Of course, the housing 32 may be made in any size, shape, style, or configuration and in some embodiments where the sanitizer itself is hidden or protected, it of course may be formed without a housing. The base 40 of the housing 32 may also be configured in any size, shape, or configuration and may be formed to fit to or attach to a variety of surfaces including contoured surfaces. However, as illustrated in the Figures, the base 40 is generally formed to mount to flat surfaces such as to the back of a cabinet, given the current desired location of the ion generation assembly 61. The base 40 is generally used to mount the sanitizer 30 to another surface 10 such as a door, wall, fixture, or proximate to any other surface or fixture requiring sanitization. The base allows easy mounting of the sanitizer to any type of surface. Of course, it is possible to mount the sanitizer 30 out of sight yet proximate to the surface being sanitized without requiring certain portions of the housing 32, as illustrated in the Figures with a mounting under the sink such as in a cabinet. In addition, the base 40 may be configured to retain a variety of different sizes, shapes, and configurations of the ion generator.

The ion source assembly 31 may be made in almost any size, shape, style or configuration and may be located surrounding handles, faucets 12, and other fixtures 10 or appliances including acting as the base 14 of a faucet or appliance such as a countertop appliance to provide a field of ions to sanitize the desired surfaces. As discussed in further detail below, the actual ion sources 82 on an ion electrode 80 are formed with particular sizes and shapes to allow maximum efficiency in producing ions; however, the general and overall size, shape, style, and configuration may be set to fit the desired surface being sanitized. Therefore, as illustrated in the Figures, the ion source assembly 61 may be formed in a round shape, elliptical shape, rectangular shape, or any other type of shape desired, or as a base 14 matching the size, shape or configuration of the associated fixture.

As illustrated in FIGS. 14-19, the sanitizer 30 may include a lens 34 or an opening on the housing 32 which allows motion to be sensed, initiating the process of sanitizing. For example, if the sanitizer 30 is placed on a refrigerator as in FIG. 14, a soap dispenser in FIGS. 17-19, or a shower head in FIGS. 20-21, the approach of a person and placing the hands under the outlets may activate the sanitizer 30. The sanitizer 30 may provide a visual or audible feedback when activated, such as through illumination of a green light or other mechanism. The sanitizer 30 may include a visual or audible warning when function is impaired or the battery life is near the end of its life. In addition, a light pipe, such as a ring in the sanitizer 30 may provide an indicator of proper function, such as a blue or green diode directed through the light pipe. To save energy, the diode may be pulsed, yet to a person viewing it, it looks constantly on. Instead of photo cell sensors or motion detectors, the controller may include a simple switch or a tab to be pressed by users to activate the sanitizer 30. An accelerometer can detect motion when sanitizing items other than hands, such as door handles, appliance surfaces and the like, and other types of fixtures as well and an accelerometer causes less battery drain than a motion detector or photo cell. For example, upon swinging open the door when someone enters a restroom, the accelerometer would be triggered which would cause the sanitizer 30 to activate for a specified time period. Therefore, when the person leaves the restroom, the door handle has been sufficiently sanitized, and typically has had sufficient time to dry from any residual liquid from the sanitizer 30. In addition, the opening of the door upon exiting the restroom would also trigger the accelerometer and activation of the sanitizer 30 sanitizing the door handle after the person leaves. Because the sanitizer 30 only functions during use of the restroom, specifically motion of the door, battery life is conserved.

For the sanitizer illustrated in FIGS. 6-13, while the ion source assembly 61 may include a lens or other mechanism for sensing motion such as a person approaching the handle of the fixture 10 such as a kitchen sink faucet 12, and thereby activate the sanitizer 30, it is expected due to the low power draw of the ion generator 60 of the present invention, and the general availability of power from the building's power supply underneath cabinets or other areas the split sanitizer 30 allows that the sanitizer 30 will be in operation at all times or on a timed basis instead of motion activated. Also given the nature of the ion generation assembly 61 being remote from the ion source assembly 31, the ion generation assembly 61 may be secured within cabinets or other places out of sight and allows more room for additional batteries and the like if the building's power supply is not available for use, is difficult to connect to, or the regulatory burden related to such connection is too high. The reference to buildings is general and the sanitizer 30 may be located in and receive power from any type of source such as an RV, outdoor venue and the like and the ion sanitizer 30 generally should not be limited to use in buildings. For example, the ion source assembly 31 may also be configured to ring either an outdoor drinking fountain's spout or the handle which is turned or pressed to activate the drinking fountain. It may ring door handles, be installed near elevator buttons and escalator handrails, and much, much more. In some embodiments, the power supply may be a rechargeable battery that is charged by the passage of water, such as with the above mentioned drinking fountain.

The sanitizer 30 does not include a puff of compressed gas or other types of actions to move the ions away but instead surprisingly uses the electronic field of the ions, in a pulsed or wave pattern. To ensure the sanitizer is working and since there is no audible perception since the sanitizer is silent, the sanitizer may include a visual or audible warning when function is impaired or the battery life is near the end of its life, if not connected to a building's power supply. For example, an LED (although not illustrated) may be included on the ion source assembly 31 and provide indication of when the sanitizer is operational. The indicator may also be a light pipe such as a ring in the sanitizer to provide indicator of proper function and various colors of blue, green, or red diodes may be provided directly or directed through the light pipe. The indicator may be formed as part of the ion electrode, such as illustrated with the flexible ion electrode in FIG. 29 which combines both the ion electrode 80 and indicator LEDs 190 into a single unit. Of course, the size, style and configuration of the flexible ion electrode 80 in FIGS. 27-29 may vary. As illustrated in FIG. 28, the flexible strip may be configured to include a ground electrode 90. If operating on battery, the indicator such as the LED may be pulsed in such a fashion that a person viewing it leaves it as constantly on but instead is pulsed to save energy. To further save energy, the source assembly 31 may be configured to detect when the fixture 10 or surface 8 being sanitized is used and activate the sanitizer for some time period after such use thereby sufficiently sanitizing the fixture 10 or surface 8. Because the sanitizer 30 only functions during use and for some time after use, battery life would be conserved if a readily available power supply from a building or other source is not available.

FIG. 1 illustrates a sanitizer 30 including the ion generation assembly 61 and the source assembly 31 interconnected with a cord 33. The illustrated sanitizer 30 includes the source assembly 31 being remote from the ion generation assembly 61 and is configured to provide an electrical field to move the ions and sufficiently sanitize a fixture 10 such as a faucet 12 without the use of fans, compressed gas cartridges and the like. More specifically, the sanitizer 30 uses a low frequency AC current applied to the electrode 70 containing the ion sources 82. The electrode 70 that includes the ion sources 82 is also herein referred to as the ion electrode 80. The ion sources 82 are illustrated as small points 84 but could be carbon fiber brushes or the like which include many tips, each acting as an ion source 82 in place of the points 84. In the sanitizer 30 that includes an ion electrode 80 having an applied AC current, an optional second electrode also may be referred to as the reference or ground electrode 90 and is included in the source assembly 61 spaced some distance apart from the ion electrode 80, or can be part of the fixture 10. The spacing of the ion electrode 80 from the reference or ground electrode 90 is specifically configured to prevent the generation of ozone or arcing. As illustrated, the ion electrode 80 is fit within a groove or recess on the source assembly to provide a tortious pathway that prevents arcing as described further below. With the ion electrode 90 being recessed, the ground electrode 90 and ion electrode 80 may be in closer proximity than across a flat surface. As described in more detail later, as the AC current is applied to the ion electrode 80 with 1-80 $H_z$, preferably a 5-70 $H_z$, more preferably 10-60 $H_z$ of alternating current ions are produced. The ion electrode is in turn driven by a transformer cycling at a high frequency, such as 20-400 $kH_z$ on and off in either the positive or negative direction, typically in the higher end of the range. The ions, both positive and negative, leave the tips of the ion sources 82 on the ion electrode 80 and are pulsed outward until they cover the desired surface. Of course, they may be assisted by other methods, such as compressed gas, fans, or the like. In addition, in some embodiments, the ions emitted from the ion sources 82 may be drawn to the ground electrode 90 which helps them in the design, illustrated in the Figures, move across the hands or fixture located between the two electrodes specifically, the ion electrode 80 to the ground electrode 90. The high frequency AC sanitizer 30 generally has a voltage of 4,000-75,000V, preferably 6,000V, when voltage is measured by the root mean square (RMS) method. The current output is typically 0.0002 amps and input will vary with the power source, typically 40-200 milliamps for most batteries. The input voltage may vary but is expected to be between 9-24V DC although 6-40V may be common. For example, in the faucet illustrated in FIG. 1, the handle of the faucet could be configured to be the reference or ground electrode or the screw holding the faucet handle on in FIG. 28 may be configured to be the reference or ground electrode. This will helps draw the ions across the relevant surfaces as they are pulsed outward, particularly across the handle that people touch.

The inventors have surprisingly found that no specific ground electrode is required for the sanitizer to function properly. Originally, that ground electrode 90 was placed in close proximity to the ion electrode 80, but of sufficient distance to prevent the generation of ozone. Then inventors surprisingly found that the ground electrode could be located as part of the fixture using the developed ion generator. Then even more surprising, with a remote ion generator assembly, such as being under a cabinet, if was found that a ground electrode on the controller 66 or housing 32 surprisingly worked as well, even though it was well spaced from the ion electrode with intervening object, such as sinks and countertops. Then even more surprising, the inventors found that an ion generator assembly connected to an external power source could use the reference ground line in such external power source to act as the ground electrode, and still get even better coverage of ions.

Figure 4:
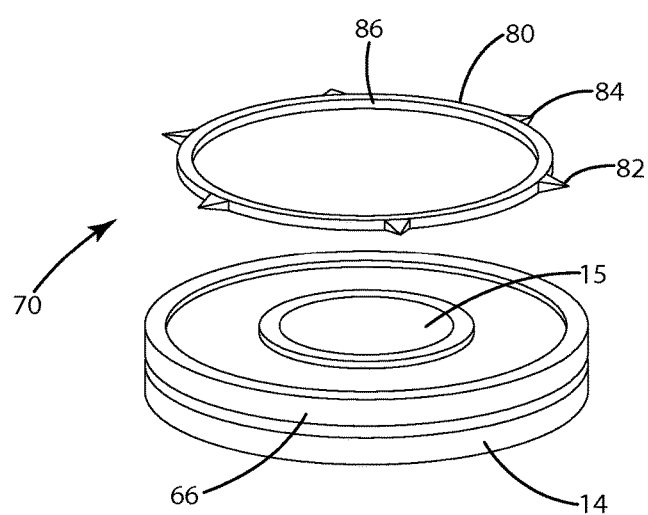
FIG. 4 is an enlarged exploded partial perspective view of an ion source assembly.
Figure 5:
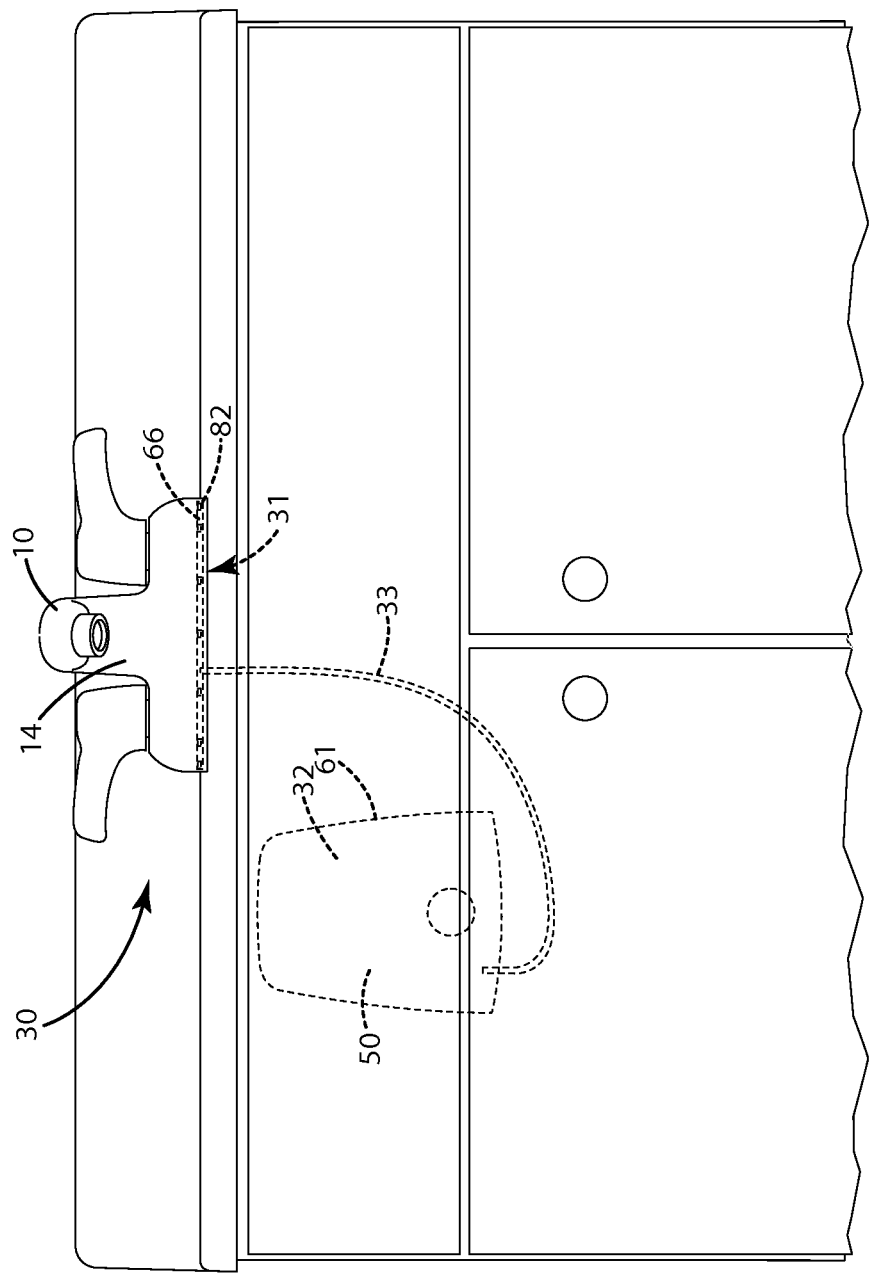
FIG. 5 is a front elevational view of the sanitizer and sink cabinet of FIG. 1 with the ion generator assembly of the sanitizer being shown in hidden lines.
Figure 6:
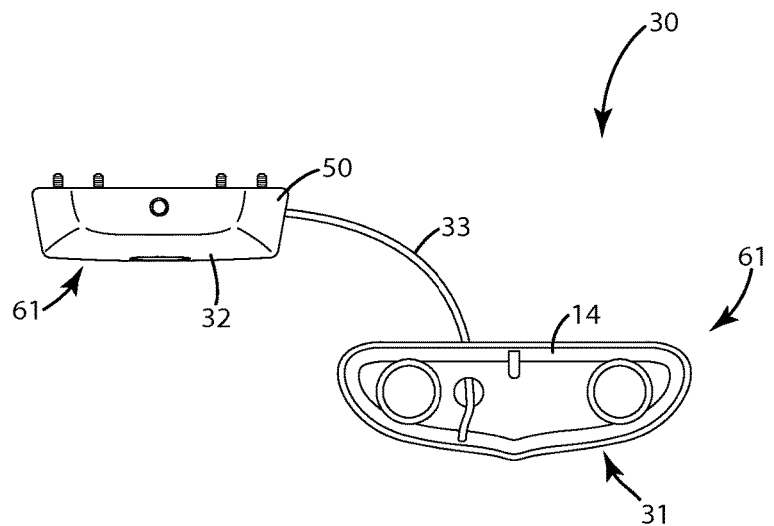
FIG. 6 is a top plan view of the sanitizer in FIG. 5.
Figure 7:
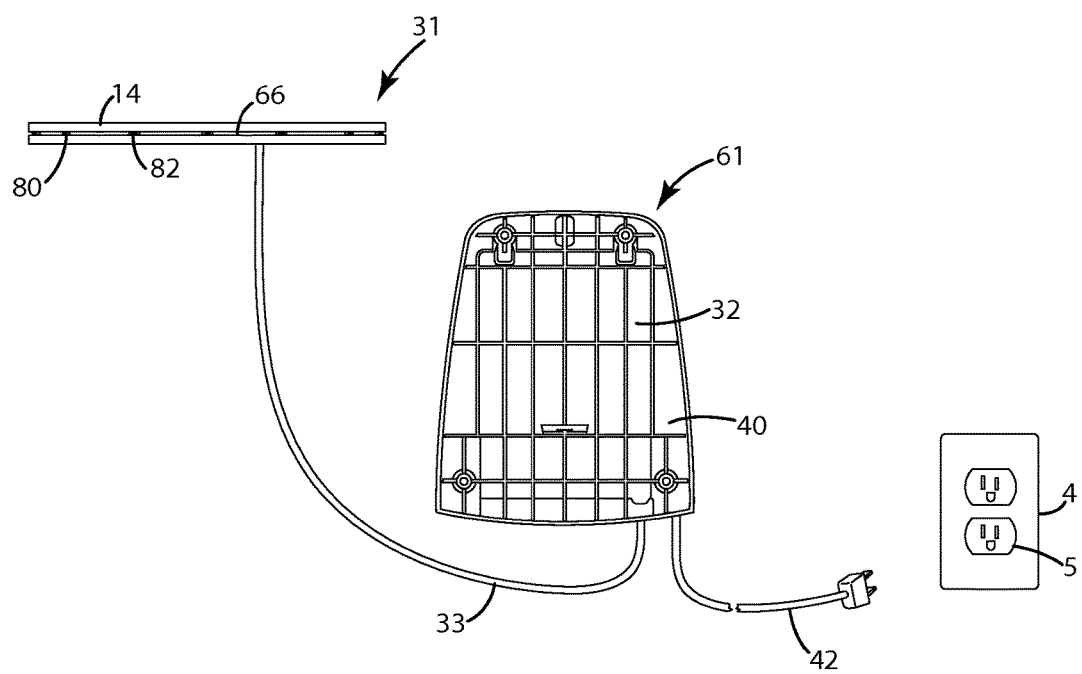
FIG. 7 is a rear elevational view of the sanitizer in FIG. 5, including an external power supply.
Figure 8:
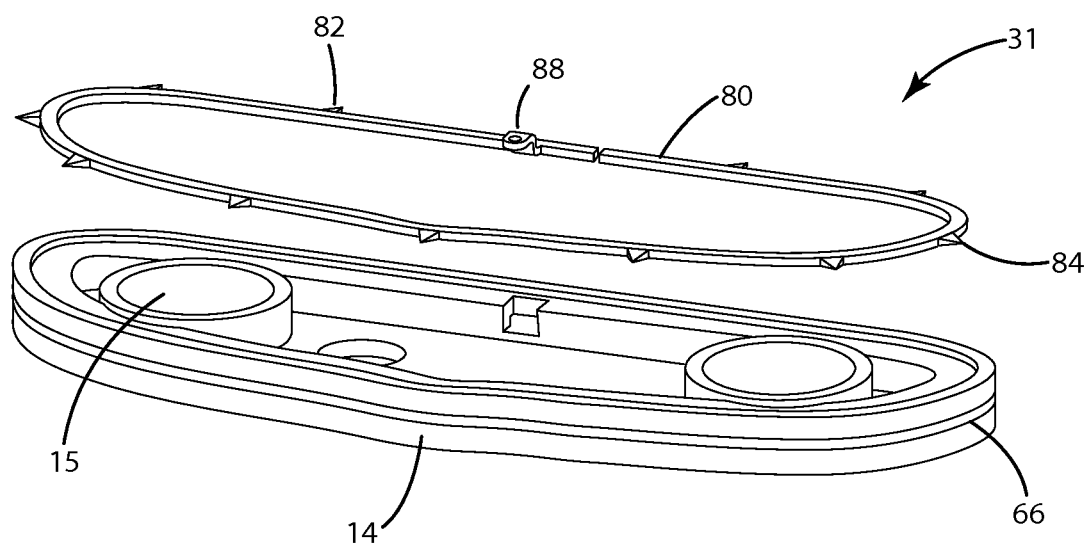
FIG. 8 is an enlarged exploded partial perspective view of an ion source assembly.
Figure 9:
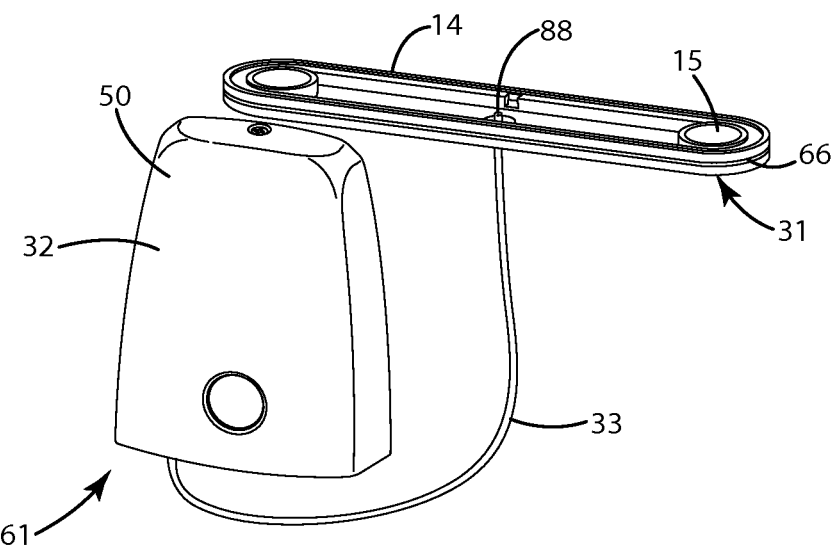
FIG. 9 is a front top perspective view of a sanitizer configured for use with a large base faucet such as a kitchen faucet having multiple entries.
Figure 12:
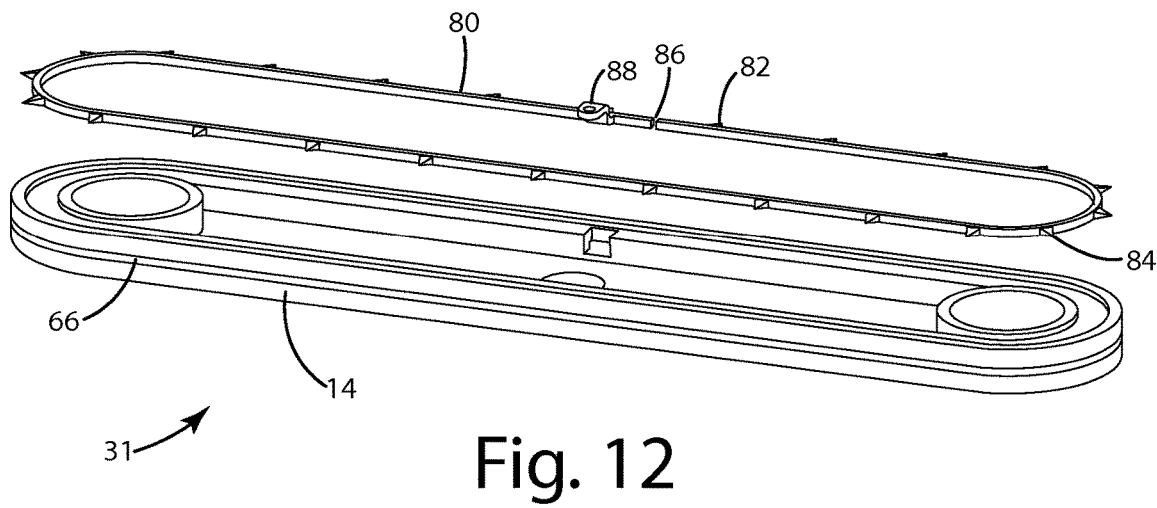
FIG. 12 is an enlarged exploded partial perspective view of an ion source assembly.

As illustrated in FIGS. 4, 8 and 12, the ion source assembly 31 has a nonconductive base and an ion electrode 80 with ion sources 82, illustrated as the points 82 on the ion electrode. As illustrated in the other Figures, the ion electrode 80 is assembled into a groove on a base 14 of the source assembly 31, which can also be an integral part of the fixture 10. The base 14 of the source assembly 31 could be also formed from a conductive material, so long as the ion electrode 80 was insulated from the base 14. As further illustrated in FIGS. 15 and 16, the sanitizer 30 which his one unit generally includes a base 40 and cover 50 as part of the housing 30 in which the sanitizing apparatus, including a battery 62, controller 64, and electrodes 80, 90, is secured and a cover 50 placed over such components and secured to the base 40. The base 40 may include cavities for a battery compartment 54 and a controller cavity 56 as well as other cavities for receiving electrodes 80, 90, such as the illustrated electrode cavities 58. The electrodes 80, 90 are connected to the controller 64 with connectors or electrical leads.

Figure 15:
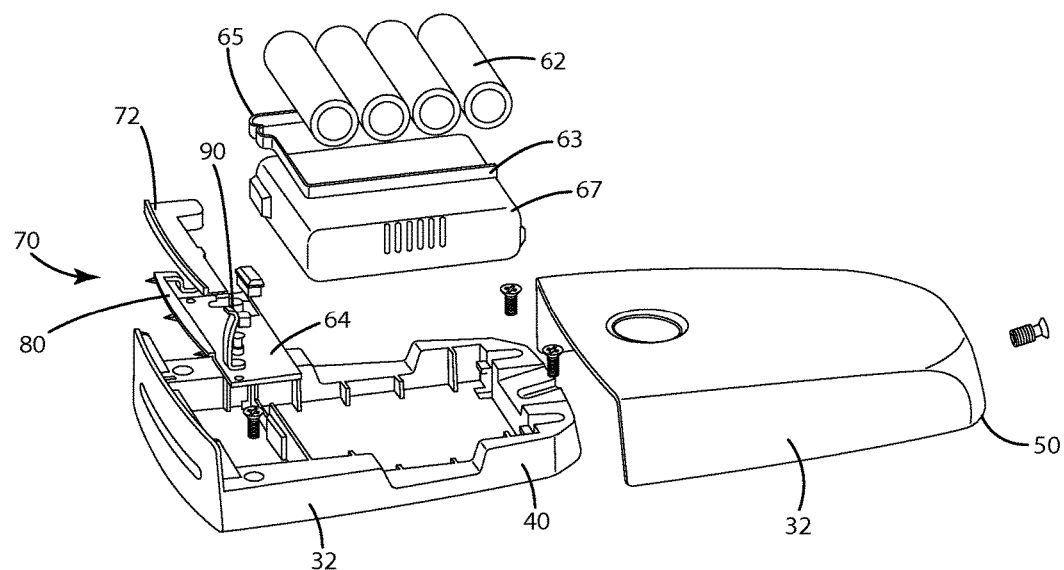
FIG. 15 is an exploded perspective view of a self-contained sanitizer that is battery powered.
Figure 16:
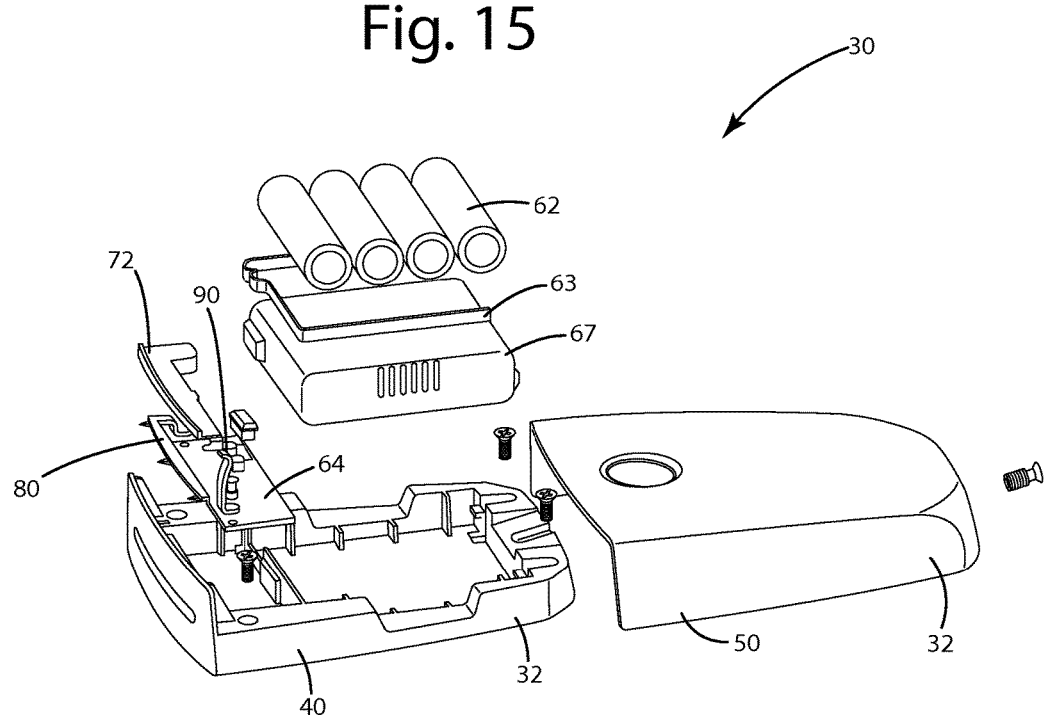
FIG. 16 is an exploded perspective view of a self-contained sanitizer that is batter powered.

The generation assembly 61 typically includes a base 40 and cover 50 in which the ion generator 60 which may include battery 62 or other power supply, controller 64, and electrical leads is secured and covered with the cover 50 of the housing 32 to the base 40. The base 40 may include cavities configured to receive the controller 64, circuit boards, and other relevant parts of the ion generator assembly 61. The ion generator assembly 61, with an exploded view is illustrated in FIGS. 15 and 16. FIGS. 15 and 16 show the ion electrode 80 built within the housing 30, however as illustrated in the other Figures, this can be replaced with the electrical lead, and ion source assembly 31 to provide the ion electrode 80 remote from the ion generator assembly 61. As illustrated in FIGS. 15 and 16, the ion generator assembly 61 includes a battery 62, a nonconductive plastic cover 50, an ion electrode 80 including ion sources 82, a batter connector 63, battery terminal 65 and a battery case 67. A circuit board is included as the controller 62 for the ion generator assembly 61. While the housing 32 cover 50 is formed from a metal material, or conductive plastic material, for the sanitizer illustrated in FIGS. 15 and 16, the cover 50 acts as the ground or reference electrode 90. Of course, other ground or reference electrodes may be provided, allowing the cover 50 to be made out of typical nonconductive plastic. For the remote ion source assembly 31 configuration, the cover 50 does not generally act as the ground or reference electrode 80, as it is located within the cabinet and remote from the ion source assembly 31 and therefore remote from the ion electrode 80.

The sanitizer 30 may include two ion electrodes 80 and eliminate the reference or ground electrode. The use of two ion electrodes 80, each including ion sources 82, has a sanitizing apparatus that uses a pulsed DC of typically 3,000-7,500 volts typically 6,000 volts is applied to each electrode 80 with, for example, one of the electrodes 80 emitting positive ions while the opposing electrode 80 emits negative ions. As such, the ions are drawn across the gap and any object in such a gap, between the two ion electrodes 80 as the electrical field propels the ions toward the opposing electrode 80. A microprocessor controls the pulsed DC.

The pulsed DC voltage may, for example, be produced by controlling a pair of transistors separately with pulse width (PWM) modulated signals from separate outputs of the microprocessor. Each transistor is used to energize the primary coil of a flyback transformer (e.g., one transformer and flyback transformer for the positive electrode and one transformer and flyback transformer for the negative electrode). When the transformer is switched off by the PWM signal from the microprocessor, the current in the primary coil and the magnetic flux drops. The voltage in the secondary coil becomes positive and current can then flow from the flyback transformer and create a voltage output at the electrode 80.

Figure 3:
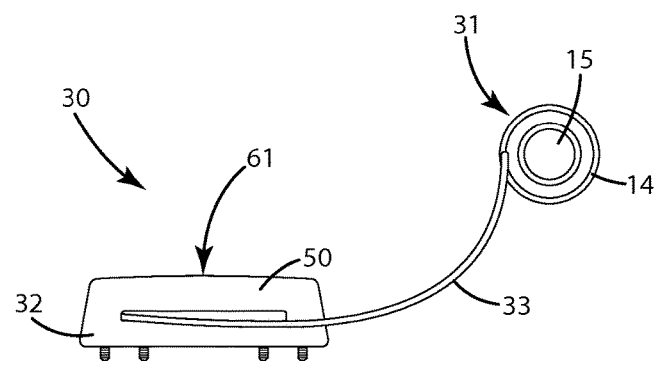
FIG. 3 is a bottom plan view of the sanitizer in FIG. 2.
Figure 34:
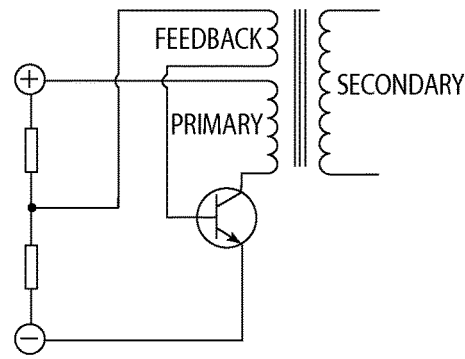
FIG. 34 is a schematic diagram of a flyback convertor using primary feedback to resonate.
Figure 35:
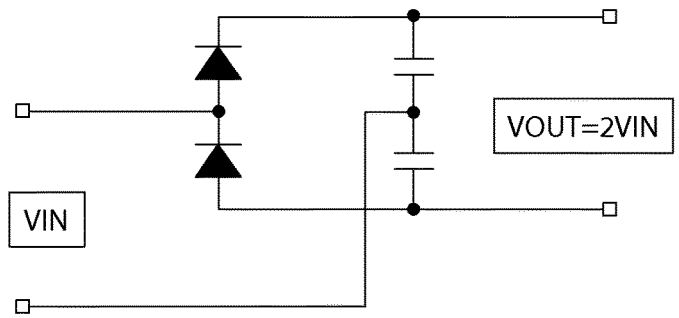
FIG. 35 is a voltage multiplier circuit which can be repeated for $V_{OUT}=X \cdot VIN$.
Figure 36:
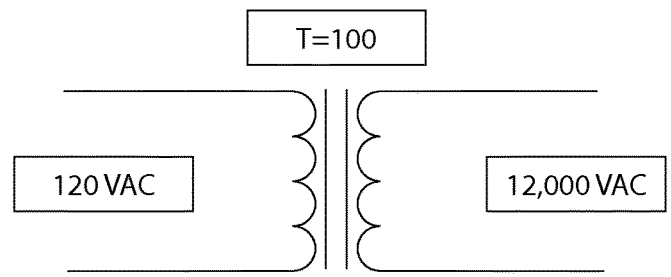
FIG. 36 is a step up transformer for high voltage AC supply.
Figure 37:
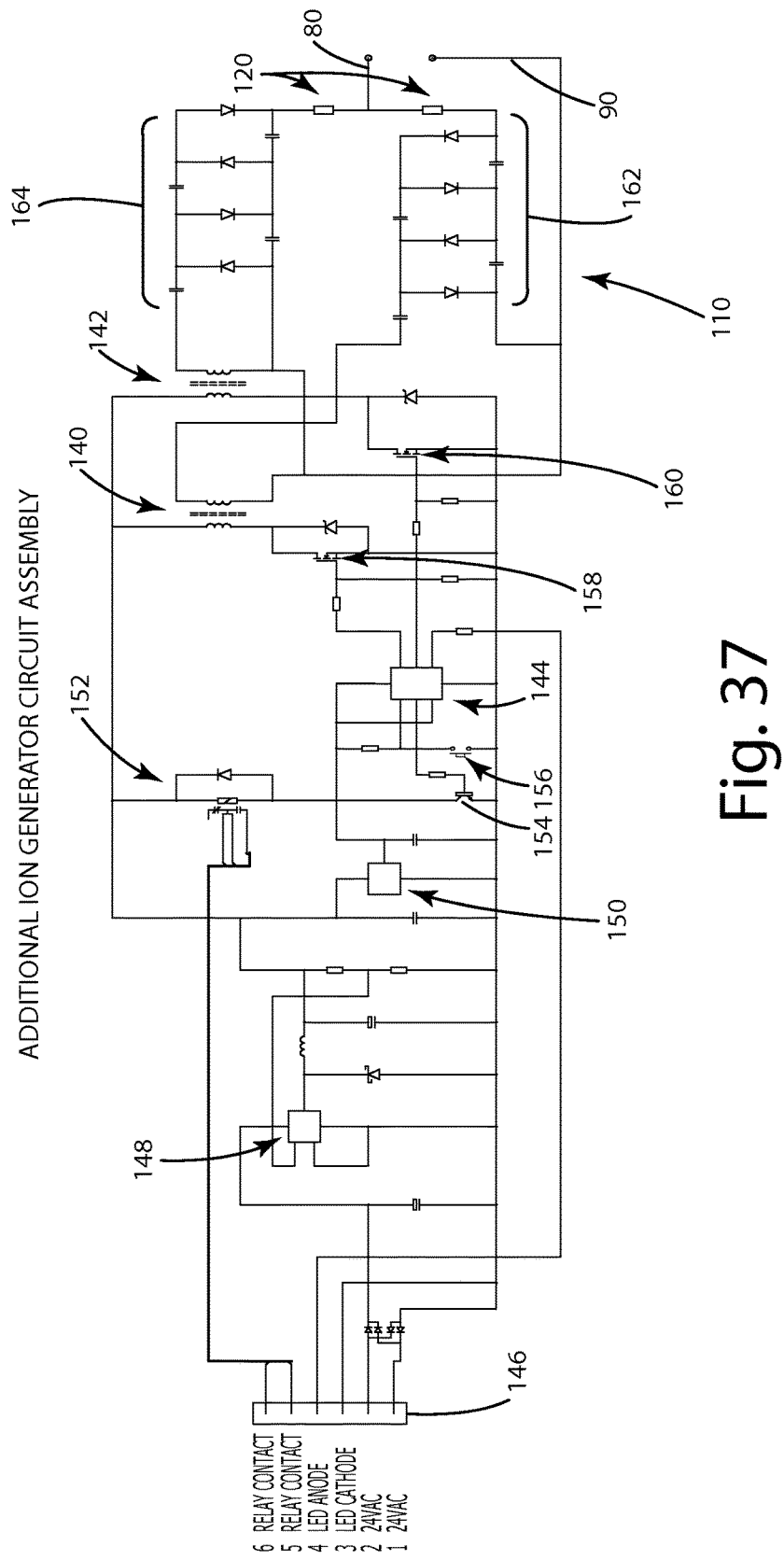
FIG. 37 is a schematic diagram of an alternative ion generator using two flyback transformers for AC output.
Figure 38:
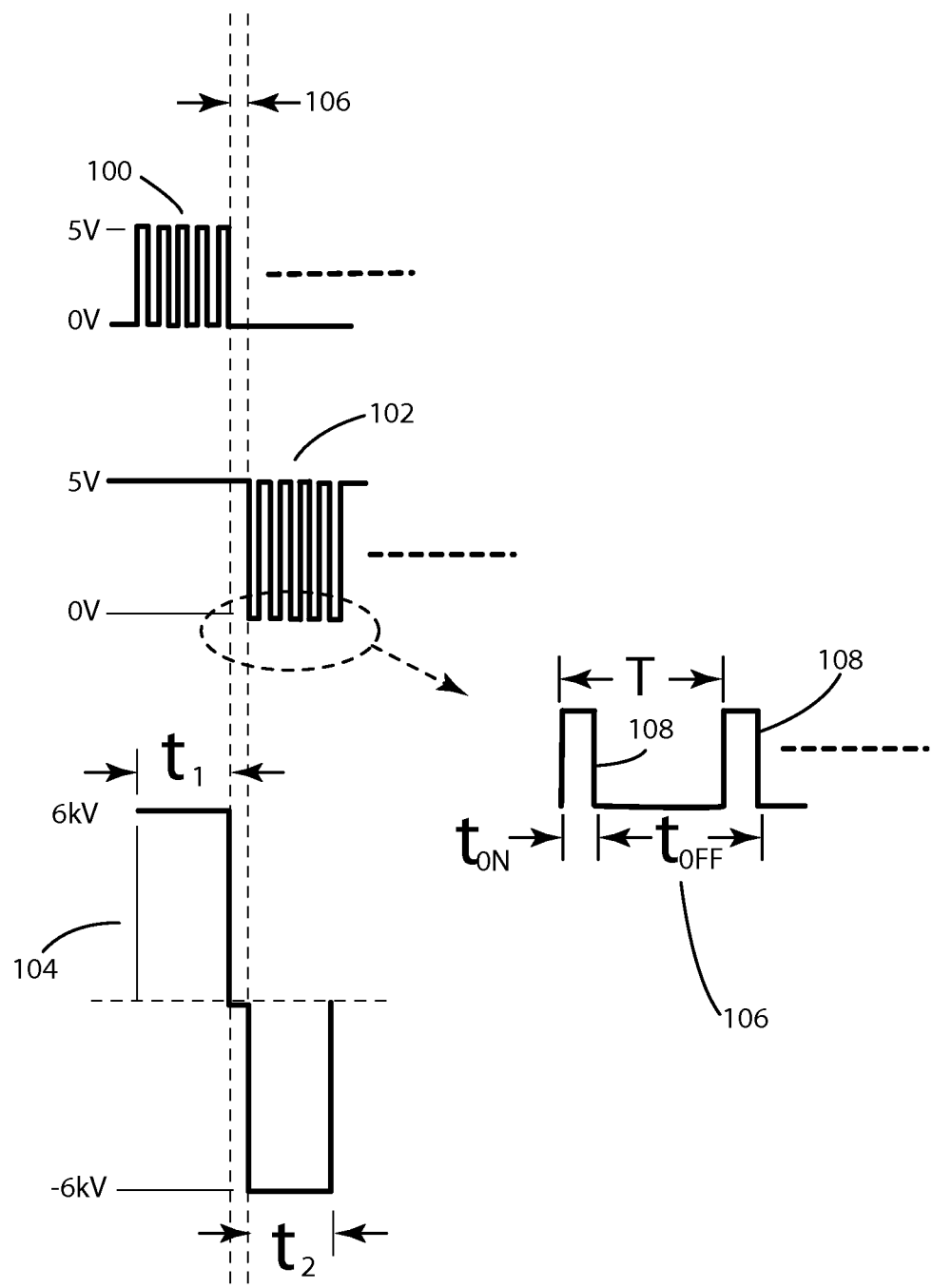
FIG. 38 illustrates an exemplary first drive signal and second drive signal and resulting high voltage AC voltage output.

One electrode 80 of the sanitizer 30 of FIG. 3 may be connected to the secondaries of both flyback transformers so that a single electrode 80 produces both positive and negative ions from an AC output and the other electrode 80 may function as a ground. As shown in FIG. 34, a first drive signal 100 or PWM pulse train which will be described in more detail below drives the first flyback transformer to create the positive half of the AC output Likewise, a second drive signal 102 or PWM pulse train drives the negative half of the AC output 104. The inventors have discovered that a "Dead Zone" 106 or period of time where both PWM pulse trains (i.e. first drive signal and second drive signal) are turned off is useful for efficient operation. Without a dead zone 106, the output from the flyback transformer driven by the first drive signal 100 may "shoot through" the flyback transformer circuit driven by the second drive signal 102 and vice versa. This may cause the outputs from each flyback transformer to somewhat cancel each other out. Adding a correctly sized dead zone 106 was shown to double the operating efficiency of the circuit. In other words, the voltage of the AC output 106 doubled while using the same amount of power.

Additionally, the level of ionization was found to increase significantly with the addition of a "Dead Zone" 106. It is thought that an abbacy change at a sharp discharge point 84 (needle point) causes emitted positive ions to combine and neutralize some of the negative ions that were emitted in the previous cycle and vice versa.

For electrical efficiency, the dead zone 106 must be a long enough time period for the previous half cycle output of the transformers energy to be dissipated and reach zero volts. The amount of energy that is initially stored in the flyback transformer by a $t_{on}$ pulse 108 shown in FIG. 34 and the transformer circuits characteristics (inductance, DC resistance and capacitance) determine the required duration of the dead zone 106. In one example, the dead zone 106 should be no less than 2 microseconds and no more than 20 microseconds.

For ion generating efficiency, the duration of the dead zone 106 is longer that what is required for electrical efficiency. The duration of the dead zone 106 for optimum ion generating efficiency also depends on the velocity of the air passing by the discharge point(s) 84. If the air is still (velocity=0) then a large dead zone 106 is required. If the velocity of the air passing over the discharge point(s) 84 is great, a smaller dead zone is required. The inventors have found a dead zone 106 of 50-100 ms is optimal. With high velocity air such as a high speed hand dryer (185 MPH) or the $CO_2$ powered door handle sanitizer smaller dead zone of 2-10 ms is optimal.

The first drive signal 100 is a pulse width modulated, PWM drive signal from the microprocessor to a circuit that produces the positive half of the AC output 104. The first drive signal 100 will be active while the second drive signal 102 is off. The first drive signal 100 is operated at a frequency between 20 KHz to 400 KHz depending on the characteristics of the flyback transformer being used. Ideally, a small flyback transformer with very low primary DC resistance and very low inductance is more energy and cost efficient and can be driven at a higher frequency. However, it has been found that the circuit works well with larger flyback transformers at the lower frequency range shown. The second drive signal 102 is similar to the first drive signal, except it drives the negative half cycle of the AC output 104.

The high voltage AC output 104 is shown in FIG. 34 as it relates to the two drive signals 100, 102 and the dead zone 106. Although, the AC output 106 is shown with a peak voltage of 6 KV, this can be varied from 2.5 KV to 12 KV by changing the PWM of the first drive signal 100 and the second drive signal 102.

The period of the drive signals 102, 104 is T. The period, T is inversely proportional to the frequency, f (T=1/f). The duty cycle is defined as the relationship between on time ($t_{on}$) and off time ($t_{off}$) during one period (T). Because flyback transformers operating in discontinuous mode, (i.e. the current in the secondary of each flyback transformer is allowed to discharge completely to zero) the duty cycle should be less than 50%—meaning that off time is greater than on time. Typically, the duty cycle approaches 50% to achieve maximum voltage output. However, the inventors unexpectedly discovered that it is not necessary and even detrimental for the duty cycle to approach 50%. This is because it is necessary to utilize sufficient off time for the transformer circuit (transformer and voltage multiplier) to fully discharge before applying another pulse. In one example, it was discovered that a duty cycle of 10% resulted in maximum AC output 104 voltage. The duty cycle may be reduced as low as 2% to adjust the AC output 104 to its minimum.

The first drive signal 100 and second drive 102 signal may also be comprised of signals having different duty cycles. For example, if the duty cycle for the first drive signal 100 is 20% and the duty cycle for the second drive signal 102 is 30% a balance of more negative ions than positive ions may be achieved, which is beneficial for human wellness. Also, in an indoor environment with lower air quality, more negative ions may get "used up" and therefore, the negative ion output may need to be increased further compared to the positive ion output. In another example, if the air is passing through a duct that has a negative surface charge, (static electricity) more positive ions may need to be created as compared to the amount of negative ions being produced.

Of course, the electrodes 70 as illustrated as the ion electrode 80, and if include, the ground electrode 90, may be made in a variety of other configurations such that the electrodes 80, 90 may surround appliance handles, touch pads, other appliance devices, stove knobs, sink faucets as well as handles and soap dispensers, doors, keypads and any other fixture or device that is touched on a regular basis that may contain bacterial, infectious diseases or other pathogens which are undesirable and preferably sanitized from such surface. The electrode 80 may also be built into various phones, tablets, computers, including surrounding keyboards and other stuff that have a high incident of infectious diseases. The sanitizer 30 may also be used proximate to other items receiving high frequency of touches or uses, such as vending machines, card readers, credit card payment devices and many other devices other than the illustrated kitchen sink faucets.

The illustrated sanitizing apparatus generally includes a battery 62 and a control circuit such as the illustrated controller 64. The electrodes 80, 90, as illustrated, are formed of a conductive plastic material such as a conductive ABS material but of course could be formed of other conductive plastics such as a conductive polycarbonate or a blend of ABS and polycarbonate. In addition, the electrode 80, 90 could be formed of metal including stainless steel, aluminum, nickel or other metals and metal alloys. Forming the electrodes 80, 90 of a plastic material allows molding of electrodes including, as illustrated in the Figures, molding the electrodes in place directly to the circuit board, specifically the controller 64. The present invention uses a conductive ABS material that has been doped with carbon but also could be doped with other materials, such as 15% stainless steel. Use of a conductive ABS allows a cost-effective material that is flexible and easy to assemble. Other cost-effective conductive polymers include conductive polypropylene, doped with carbon, boron, or the like. In addition, using a conductive plastic avoids potential corrosion of metal electrodes and many of the harsh environments where sanitizers 30 are desirable to be placed. For example, in a restroom, humidity as well as harsh cleaning supplies are regularly applied or incurred by fixtures, including the sanitizer 30 within the restroom and after a certain time period, even stainless steel may corrode.

Figure 10:
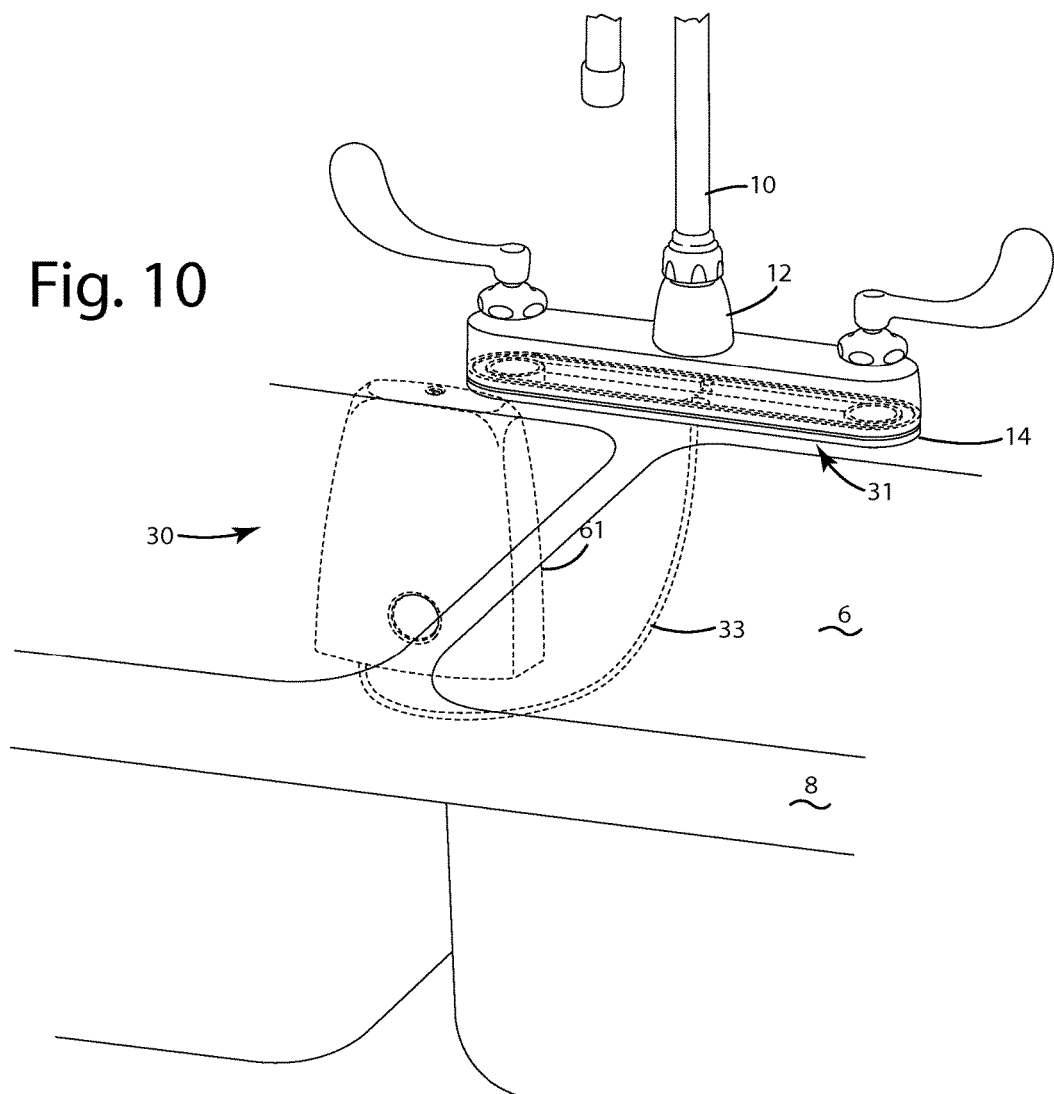
FIG. 10 is a top perspective view of a sanitizer utilized with a kitchen sink faucet.
Figure 11:
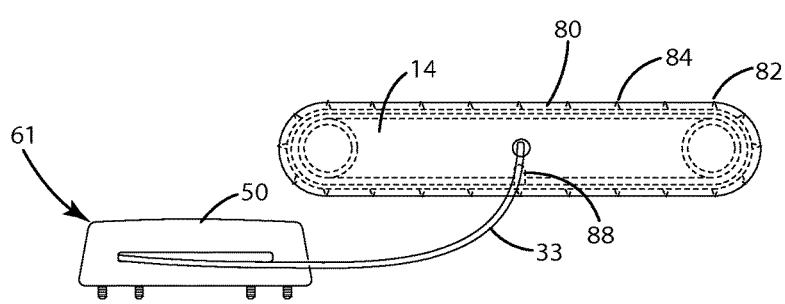
FIG. 11 is a bottom plan view of the sanitizer.

The housing 32, including the base 40 and cover 50 is generally formed from a non-conductive material to prevent the cover 50 from being electrically conductive with the electrodes. Of course, the housing 32 may be formed from metal or other materials if the electrodes are insulated from the housing 32. The electrodes are injection molded, although other methods may be used. To obtain the points 84, as illustrated in FIGS. 10-12, which is not possible with injection molding, given the size of the points 84, the dies are scored to create flash at the points, which creates the pointed surface the present invention uses to create the ions. The illustrated points 84 protrude about 4 mm from the electrode base 40, which is illustrated as about 4 mm wide and 1.6 mm thick, although other dimensions could be substituted. The points 84 of the electrode 80, forming the ion sources 82, are recessed in the sanitizer 30 to avoid contact with humans. In the present invention, the ion sources 82 are generally spaced more than a ¼" or 6 mm apart, but less than 2" or 50 mm apart. It has been found that the pulse effect to drive the ions away from the ion sources 82 at less than ¼" apart generally causes the ions to cancel each other out and at more than 2" apart, the ions may not be applied as uniformly to the surface 10. In the illustrated embodiment, the ion sources 82 are spaced about ½" or about 12.5 mm apart. The most effective range of spacing has been found to be about ⅜" to 1". In addition, using a conductive plastic avoids potential corrosion of metal electrodes and many of the harsh environments where sanitizers are desirable to be placed. For example, in a restroom, humidity as well as harsh cleaning supplies are regularly applied or incurred by fixtures, including the sanitizer within the restroom and after a certain time period, even stainless steel may corrode. Therefore, conductive plastic may form the electrodes.

The sanitizer 30 may be attached to a desired area through a variety of mechanisms, such as the illustrated fasteners 42. As assembled, it is desirable for the sanitizing apparatus to be unobtrusive and maintenance free as possible. Of course, as described above, the sanitizer 30 may be attached maybe directly into the fixture 20, appliance, or other surfaces 10.

Figure 17:
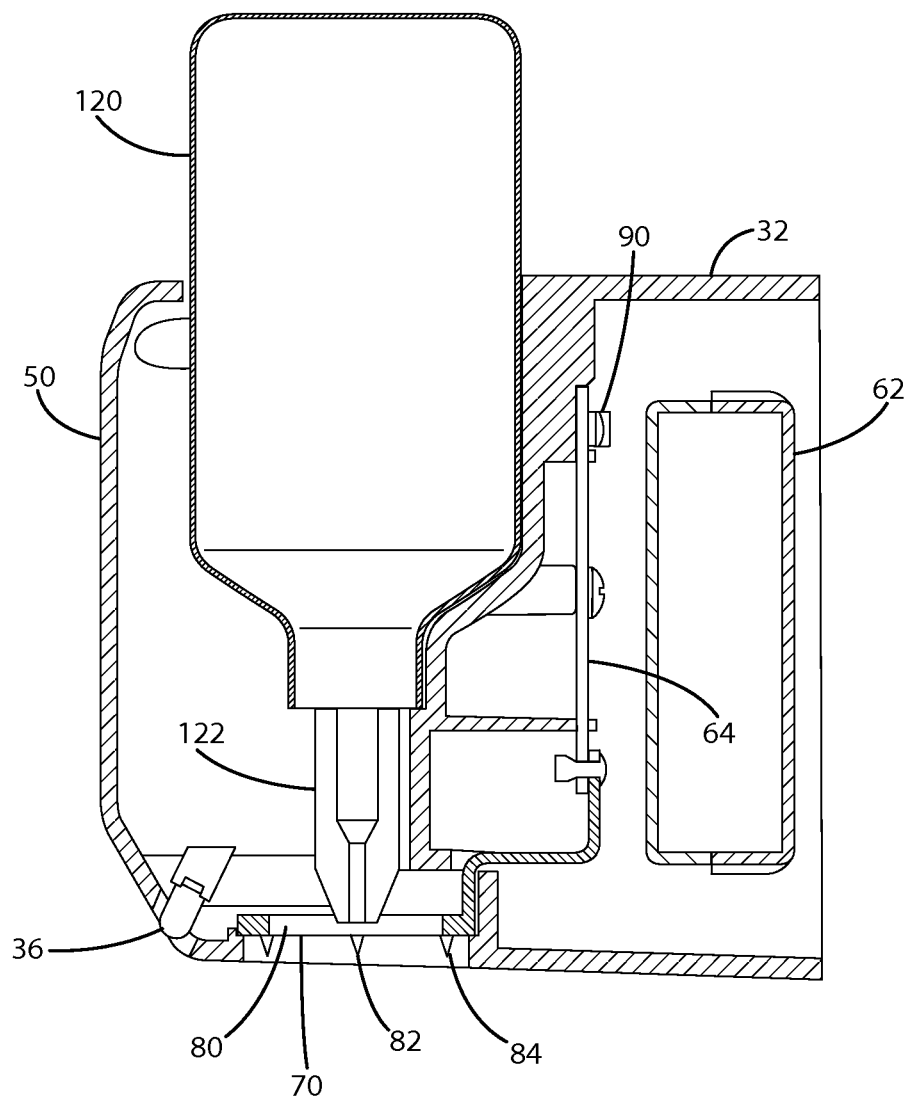
FIG. 17 is a cross sectional view of an exemplary sanitizer that include a fluid reservoir.

The sanitizer 30 as illustrated in the Figures is specifically configured to provide a wide dispersal of ions such that, even though being illustrated as centered, the fixture 10 does not need to be centered between two electrodes 80, 90 or be situated extremely close to the ion electrode 80. As such, the ion source assembly may be under one faucet handle, or the center spout for the illustrated three-piece faucet. The illustrated sanitizer 30 is illustrated as having 360° of ion sources 82 but of course, by removal of some of the ion sources 82 from the ion electrode 80, the coverage of ions may be reduced to something less than 360°. In addition, the number of ion sources 82 shown on each ion electrode 80 may vary as well as the position or placement may vary depending upon the desired application. It has been found that use of the present sanitizer 30 may provide sufficient generation and dispersal of ions across a six-foot radius area from the sanitizer 30 to substantially sanitize the surfaces or at least reduce the number of pathogens and other infectious diseases on such surfaces. For example, a restroom, kitchen, or other facility may include a number of these sanitizers secured to ceilings, countertops, or walls, thereby providing substantially continuous coverage across the whole area to sanitize or reduce the number of infectious diseases on a majority of the proximate surfaces. A liquid tank may be combined with the ionizer provides additional sanitizing capabilities, including producing certain sanitizing chemicals that are not subject to the quick recombination of the normally produced ions. A sanitizer with a liquid tank or reservoir 120 is illustrated in FIG. 17.

The illustrated sanitizer 30 in the Figures include a ground electrode 90 and as such, uses a high frequency transformer to drive an AC current applied to the ion electrode to generate the ions at the ion sources 82, if the sanitizer uses a battery as the power supply. However, where the sanitizer 30 is connected to a building or other external power supply the sanitizer 30 may use ground 5 through such power supply 4 as the ground electrode 90 thereby eliminating any separate the ground electrode. Of course, a pulsed DC version where the ground electrode 90 is swapped for an ion electrode 80 may also be used, but preferably would be placed in a setting experiencing air movement, or where a user would place their hands or object within a set proximity. Similar to the above, the electrodes 80, 90 also may be formed of a conductive plastic material such as a conductive ABS, although again, various other metals or alloys may also be used to create the electrodes 80, 90. The electrodes each include connectors allowing for easy assembly to the controller. Of course, the configuration of the sanitizer 30 and individual components therein may vary depending upon the desired application. The controller 64 is expected to be sealed with epoxy or another material. The battery 62 as used in the sanitizer 30 may be any type of battery 62, however a long-life battery such as a lithium ion battery is generally preferred. The use of a lithium ion battery allows extension of the intervals between required maintenances and replacement of the battery, as compared to more traditional batteries. Of course, the sanitizer 30 may be hardwired into the building power supply. The illustrated sanitizer 30 and source assembly 31 may be assembled through a variety of methods including where the cover 50 is capable of being split into multiple pieces and snapped together or ultrasonically welded together with the electrodes fitting within grooves on the cover 50. In addition, the ion electrode 80 and ground electrode 90 may be formed with a small split on at least one side allowing expansion of the electrodes 70 as they slide over the cover 50 and then contraction as they fit within the specified and desired groove. However, as illustrated in FIGS. 15 and 16, the ion electrode 80 may be loosely placed inside the cover 50 near the opening 51.

As illustrated in Figures, the source assembly 31 may be formed in a puck shape with the ion electrode 80 in a groove 66 on a cover 50, and the ground electrode 90 in another groove 66. If multiple grooves are used for ground electrode 90 and ion electrode 80, the grooves 66 on the cover 50 are spaced about 10-20 mm, preferably 10-15 mm, apart and the recesses forming the grooves 66 are about 14 mm deep, with the point 84 being recessed 3 mm from the surface. Therefore, the groove 66 allows closer spacing of electrodes 80, 90 and a smaller package to the source assembly 31. However, the depth of the groove 66 relative to the spacing of the grooves 66 is also important as too deep of a groove 66 may prevent sufficient expulsion of the ions from the groove 66. As the electrodes 80, 90 are more recessed in the grooves 66, the spacing of the grooves 66 may shrink and as the electrodes 80, 90 approach the surface of the cover 50, the spacing of the grooves 66 increases to prevent arcing and ozone generation.

The battery 62 may also be rechargeable, and the sanitizer could include a USB port or other input that could provide charge to the battery 62. In addition, the device may include Bluetooth or Wi-Fi to allow control of the device with smartphones, computer, tablets, and the like, or for a person to check the status of all devices within a facility or within a given range. Control over the voltage output, and as such amount of ions generated as well as battery life could be controlled. Any inputs, such as a power supply input, USB input and the like may be covered to prevent liquid intrusion, such as if a sanitizer was used on a kitchen counter.

The ion source assembly 31, as stated above, generally includes a base 14 having a groove 66 for receiving the ion electrode 80. The points 84 or ions sources 82 on the ion electrode 80 may extend out of the groove 66, or be recessed in the groove 66. The ground or reference electrode 90, if included, may be part of the ion source assembly, but also could be part of the faucet, fixture, appliance or the like to better draw the ions across the desired surface. A controller 64 and a battery 62 may be assembled to the base 40 as part of the ion generator assembly 61 and then covered with the cover 50 for general protection, with the ion source assembly 31 and the ion generator assembly 61 being electrically coupled with the illustrated electrical lead 33. The ion generator assembly 61 can include an additional ion electrode 80 as illustrated in FIGS. 15 and 16 to sanitize under the cabinet, in addition to the fixture 10, with the ion generator assembly 61 being additionally paired with a remote ion source assembly 31.

Figure 14:
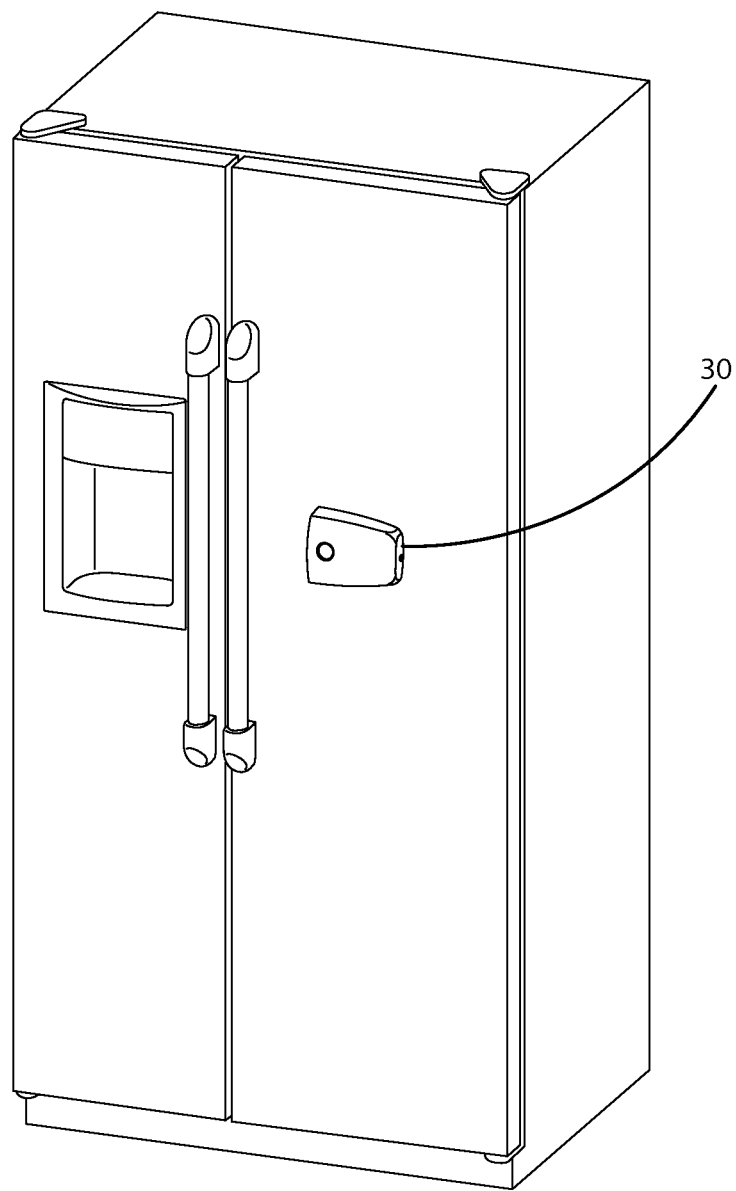
FIG. 14 is a top front perspective view of the sanitizer from FIG. 15 on a refrigerator.

In FIG. 14, the sanitizer 30 of FIGS. 15 and 16, being a single unit, is illustrated as being mounted on an appliance, such as a refrigerator surface 14. As stated above, the sanitizer of FIG. 15 may be a self-contained unit, with the ion electrode 80 recessed in the cover 50 of the housing 32. The housing 32 or base 40 may act as the ground electrode, and the ion electrode 80 is recessed within the gap. The sanitizer 30 may be battery powered. Of course, a sanitizer 30, similar to that in FIG. 1 may also be used, with the ion source assembly being formed as part of the handle or knob of an appliance, such as forming the base of the illustrated handle and be electrically in communication with the ion generation assembly, which would be hidden from view in the refrigerator, such as in the underside, back side, with the electrical lead running through the door to the ion source assembly.

While the sanitizer 30 in FIG. 15 illustrates a specific electrode 70 acting as the ground electrode 90 or ground plane, objects on the device or the sanitizer 30 could be formed as the ground plane. Generally speaking the ground electrode may be placed anywhere so long as it is not too close to the discharge points 84 on the ion electrode 80, which could cause arcing and create ozone. Ozone is specifically not desired to create. The flexibility in placing the ground electrode is actually very surprising, especially that it makes little difference in the ions generated in the plasma field, but can be helpful in drawing the ions in a particular direction. One item of care is that the ground plane must be placed or configured to avoid creating a capacitive load. For example, to sanitize proximate to the kitchen sink or faucet, one of the sink or faucet could be a ground plane for the ion generating electrode. As it is a ground plane, and naturally grounded through the plumbing, the ion generator could be configured to attach the ground electrode to the metal pipes of the plumbing or metal fixtures of the plumbing. Therefore, the faucet is the ground, and a ring or plate could extend under the faucet or around the faucet, such as a plastic insert around the faucet and includes in a recess, the ion generating electrode. It is preferable to recess the ion generating electrode 80 to prevent contact with the ion sources 82 on the ion electrode 80 and to create a torturous pathway so minimize packaging around the ion electrode 80 and spacing required to the ground electrode 90.

It is important to note that the ion generator or sanitizer 30 generally includes a large resistor such as a 50 mega ohm protection resistor 128 in the present invention, which limits the current as a safety feature and limits it to micro amps of current. The ion generator could also be used in a shower to prevent growth of mold, bacteria and other pathogens in a shower, particularly public showers or enclosed showers where humidity stays present and promotes undesirable growth. Also, the more humidity that occurs in a shower the more effective the ion generator is at generating ions and therefore more effective at greater distances.

As illustrated in FIGS. 17-19, a sanitizer 30 may be self-contained within fixture 10, such as the illustrated soap dispenser 16, such as the illustrated a battery operated sanitizer unit 30 housed within the soap dispenser 16. If no external power supply is avoidable, and as such no external ground connection, one of the base 40 or cover 50 may act as the ground electrode 90, to be used in connection with the ion electrode 80, although a ground electrode 90 may be built into other areas of the housing, such as a metal button 17 at the end of the push member that is pushed to dispense the soap.

It has been found that use of the sanitizer of the present invention as illustrated may provide sufficient generation and dispersal of ions across at least a six-foot radius area from the sanitizer 30, specifically the ion electrode 80, to substantially sanitize the surfaces or at least reduce the number of pathogens and other infectious diseases on such surfaces 8. For example, a restroom, kitchen, or other facility may include a number of these ion sources secured to ceilings, countertops, or walls, thereby providing substantially continuous coverage across the whole area to sanitize or reduce the number of infectious diseases on a majority of the proximate surfaces 8. For the illustrated faucet sanitizer 30, this allows sanitization of the counter surfaces 8 surrounding the sink 6, as well as the sink itself, which may also reduce odors associated with microbial activity in sinks and garbage disposals.

The illustrated sanitizer 30 uses a low frequency AC current applied to the ion electrode 80 to generate the ions at the ion sources 82. As stated above, if a sanitizer 30 is attached to an external power supply, the ground connection of such external power supply may act as the ground electrode, thereby eliminating the need for a separate ground electrode 90 in the sanitizer 30. Of course, even with a sanitizer 30 connected to the ground connection 5 of an external power supply 4, the sanitizer may include a specific additional ground electrode 90, which may be useful in directing ions across a surface in a controlled fashion, such as between the ion sources 82 of the ion electrode 80 toward the ground electrode. By directing the ions, the sanitizer may be configured to apply concentrated ions in certain areas instead of a more evenly spread out dispersal of the ions. Controlling the locations of the ion sources 82 may also cause ions to disperse in a directed manner. As such, the sanitizer 30 may be configured to apply ions where most needed, in a concentrated fashion, but without the typical mechanical systems, such as fans, compressed air and the like to direct the ions, all of which reduce battery life or require additional maintenance. Of course, a pulsed DC version where the ground electrode is swapped for an ion electrode may also be used.

Figure 13:
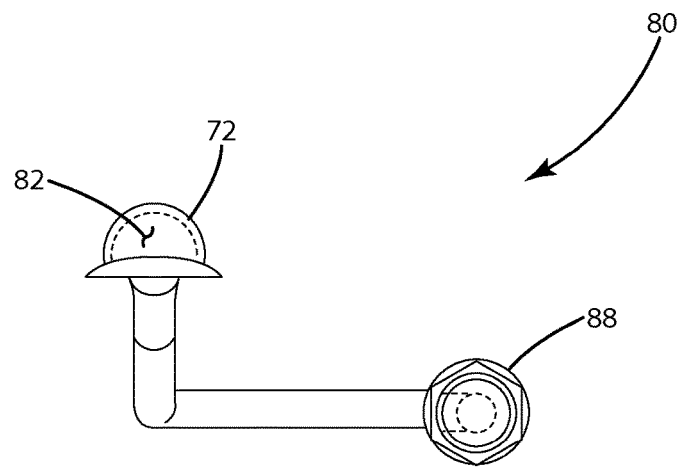
FIG. 13 is an end view of the sanitizer with a flexible electrode.

The electrodes also may be formed of a conductive plastic material such as a conductive ABS, although again, various other metals or alloys may also be used to create the electrodes. As illustrated in FIG. 13 and discussed above, the electrode may be made out of a flexible material, such as LED strips, with needles attached thereto. The electrodes each include connectors allowing for easy assembly to the controller 64. Of course, the configuration of the sanitizer 30 and individual components therein as illustrated in FIGS. may vary depending upon the desired application. The controller is expected to be sealed with epoxy or another material. The battery 62 as used in the sanitizer 30 may be any type of battery; however, a long-life battery such as a lithium ion battery is generally preferred. The use of a lithium ion battery allows extension of the intervals between required maintenances and replacement of the battery, as compared to more traditional batteries. The illustrated sanitizer in FIG. 15 may be assembled through a variety of methods including where the cover 50 or the source assembly 31 is capable of being split into multiple pieces and snapped together or ultrasonically welded together with the electrodes 80 fitting within the illustrated grooves 66 on the cover. In addition, the ion electrode 80 and ground electrode 90, if included, may be formed with a small split on at least one side allowing expansion of the electrodes 80 as they slide over the cover 50 or source assembly 31 and then contraction as they fit within the specified and desired groove 66. The inventors have surprisingly found that even though the needles or ion sources 82 may be covered, such as the groove 66 is covered to give a smooth look to the source assembly 31, or cover 50, and at the same time eliminate a groove that may attract dirt and be difficult to clean.

A single groove 66 is illustrated as the source assembly does not have a ground electrode in most Figures, however, the grooves 66 on the cover 50 or source assembly 31 are spaced about 20 mm apart and the recesses are about 14 mm deep if a ground electrode 90 is included. The electrodes 70 being recessed avoids arcing that would otherwise occur if the electrodes 70 were spaced 20 mm apart on the surface of the cover of ion source assembly 31. Therefore, the groove 66 allows closer spacing of electrodes 70 and a smaller package to the sanitizer. However, the depth of the groove 66 is relative to the spacing of the grooves 66. It is also important as too deep of a groove 66 may prevent sufficient expulsion of the ions from the groove 66. As the electrodes 70 are more recessed in the grooves 66, the spacing of the grooves 66 may shrink and as the electrodes 70 approach the surface of the cover 50, the spacing of the grooves 66 increases to prevent arcing and ozone generation.

The battery 62 may also be rechargeable, and the sanitizer 30 could include a USB port or other input that could provide charge to the battery. In addition, the device may include Bluetooth or Wi-Fi to allow control of the device with smartphones, computer, tablets, and the like, or for a person to check the status of all devices within a facility or within a given range. Control over the voltage output, and as such amount of ions generated as well as battery life could be controlled. Any inputs, such as a power supply input, USB input and the like may be covered to prevent liquid intrusion, such as if a sanitizer was used on a kitchen counter.

As discussed above, most ion generators require a means of propulsion such as compressed air or $CO_2$ to move the ions away from the ion source, however, the inventors have surprisingly found that a high voltage AC ion generator is capable, of moving the ions away from the ion sources if properly configured and operated within certain operational ranges. In addition, the AC version described herein actually is an improvement in dispensing ions without separate means of propelling ions away from the ion sources as compared to traditional DC ion generators that use two electrodes, each have any opposing charge. The ion generator of the present invention creates more ions, uses less power, particularly less power from battery packs, and expels the ions a greater distance from the ion electrode without the need for additional propulsion, such as compressed gas in sanitizers. More specifically, an alternating current (AC) high voltage source has been found to be ideal for ion generators particularly when compared to traditional DC sanitizers. However, it should be noted that the DC sanitizer with the fork design overcomes the limitations of DC sanitizers particularly with regards to the fixture cavity as illustrated in FIGS. 1 and 3. One unique feature of the present invention is that the AC high voltage ion generator only requires one discharge electrode 80, which may have one or more points 84, not two discharge electrodes of opposite polarity, yet can function as a bipolar ion generator that generates both positive and negative ions. This single discharge point or single ion electrode 80 (which can have multiple discharge points 84 along the electrode as illustrated) can alternate between creating positive and negative ions. The inventors have found that this surprisingly yields the following advantages: (1) only one discharge point 84 required to create both positive and negative ions, although a ground electrode 90 may be still used to create a ground plane; (2) by alternating polarity of the single discharge point or ion electrode 80, it is far less likely to be contaminated with dust and will therefore have greater service life, because dust particles or other contaminants are attracted to the discharge point or electrode when it is positively charged will be repelled when it is negatively charged and vice versa; and (3) the use of AC high voltage ion generator can deliver higher concentrations of positive and negative ions at a greater distance from the discharge point(s) 84. The fact that the ion generating electrode 80 does not attract dust like the positive electrode of prior DC ion generators allows a longer service life and maintains operational performance closer to original specifications over the service life of the ion generator as the dust interferes on a DC ion generator with the generation of the positive ions. However, with regards to the illustrated DC sanitizer, the inventors have found that a burst of higher discharge may burn off dust particles, and while such a discharge may create ozone, the duration would be so short and so infrequent that barely any ozone would be created and would not noticeably add to the level of ozone in the proximity of the sanitizer and be under all applicable rules or regulations regarding the discharge of ozone. In addition, typically is was believed that to generate sufficient ions, at least two electrodes having opposing chargers were required, or at a minimum a sacrificial electrode was required. In the present invention, no sacrificial electrode is required, and the single ion electrode 80 generates all of the ions, and it is believed that the alternating current and resulting alternating production of positive and negative ions generates a pulse effect, similar to the ripples in water when an object is dropped in that as small waves expand outward. In the present invention, the pulsing creates waves that cause the ions to travel away from the ion generating electrode.

While the ion generator of the present invention uses high voltage AC, which the stepped up or higher voltage AC is usually created using a step-up transformer, the step up transformer is not preferred as discussed below. In a step up transformer, a low voltage AC supply is supplied to the primary side of the transformer. The step-up transformer provides an output voltage that is equal to the input voltage multiplied by turns ratio of the step up transformer. For example, a transformer with 10 turns on the primary and 1,000 turns on the secondary has a turns ratio of 100 (T=100). If 120 VAC were applied to the input, the output voltage would be 12,000 VAC. While such a solution is simple and effective method for high voltage AC supply, it suffers from poor electrical efficiency, high cost, and large size.

Therefore, as stated above, the present invention can use a step up transformer, however the inventors have found it preferable to reduce the size of the packaging and the power loss due to heat generation. Therefore, the present invention creates high voltage AC for a single discharge point bipolar ionizer or multiple discharge points that experience the same positive or negative charge at the same time two flyback transformers 140, 142 resulting in a design which does not require the size, cost, weight, or energy consumption of a step-up transfer design. Further, the proposed design can accept a variety of AC or DC inputs to create the high voltage AC output. A simple pot can be provided to allow adjustment of the high voltage AC output for different applications. The range of AC output required to generate ions may vary, however the inventors have found that a minimum of 3000V peak to peak (e.g. +1500V to −1500V), preferably 4,000V peak to peak, and more preferably at least 5,000V peak to peak, but in no event more than 12,000V peak to peak, preferably less than 8000V peak to peak and more preferably less than 7500V peak to peak. The above voltages may vary depending on spacing and are set for the ion generating electrode 80 to be spaced between about 2 cm and 5 cm (¾"-2") from the ground plane or ground electrode 90. As such, for these spacings to avoid creating of ozone, the voltage ranges are critical, and as such, typically as the electrodes 70 are placed in closer proximity the lower end of the ranges above is preferred and as the spacing increases the higher end of the above voltage ranges is preferred. In addition, beyond strictly the distance, if the distance is a torturous pathway between the ion electrode 80 and the ground electrode 90, such as the illustrated puck design in the Figures, the voltage may be run at a higher voltage than if both of the electrodes were placed on the same surface with no intervening obstructions as the latter would be more likely to arc or create ozone. As it is best to balance power consumption and the amount of ions generating a range of voltage for the ion generating electrode to be spaced 2-5 cm from the ground electrode is typically 3,000-7,500V peak to peak, and preferably 4,000-6,000V peak to peak, and more preferably 5,000-6,000V peak to peak. As stated above, all of the voltage measurements provided are RMS voltage. As stated above, the present invention uses two flyback transformers 140, 142, one to create the positive half of a high voltage AC output and the other to create the negative half of the high voltage AC output. The two outputs are combined into a single high voltage AC output. A micro controller or microprocessor 144 is used to switch the transformers 140, 142 in a stable manner. The use of two flyback transformers that are switched also improves the output of the ion electrode 80, because the system is almost immediately at full power, maximizing production of the ions at the ion electrode 80, whereas a flyback transformer utilizing feedback from a primary or secondary coil to create a resonator does not stabilize to full power for a long period of time. FIG. 28 clearly illustrates the immediate spike in voltage over time against the square wave of the flyback transformers 140 and the slow drop off in voltage to the ion electrode 80 after the square wave has ended and then the immediate opposite jump in voltage as the square wave of the other flyback transformer 142 is applied. As the microcontroller 144 switches back and forth, the pattern is repeated. As illustrated in the Figures, a 5V input is provided and 2500 V output is then provided. Of course, other voltages, both output and input may be configured and provided.

The cycle rate between series of positive and negative peaks or drive signals 100, 102 (i.e., to provide the high voltage AC output) is preferably at least 10,000 Hz, and more preferably at least 25,000 Hz, and for the illustrated exemplary configuration in the Figures, the ion generator 110 operates at about 100,000 Hz, which provides the best balance of generating ions, low cost, and low power requirements. FIG. 23 illustrates exemplary drive signals 100, 102 and resulting high voltage AC output. It has been found that even with such quick cycling, the ions are sufficiently generated and the present invention typically uses 75,000-100,000 Hz frequency rate. It is important to note that the present invention does not use a 60 Hz cycle rate and more importantly that the present invention using an ion generator 60 operating at 100,000 Hz and 3000-7500V, preferably 5000-6000V peak to peak is operating at what many skilled in the art consider unstable and attempt to avoid. However, the inventors have surprisingly found that these parameters offer the best generation of ions, particularly when measured against the power consumption of the ion generator 60 where it is desired to maximize battery life.

The emitters are attached to a flexible circuit board (FIG. 13). The inventors have discovered that it is possible to separately manufacture flexible circuit boards, flexible strips, or to modify commercially available LED light strips to provide both LED lighting and multiple points (emitters) or alternatively to provide spaced emitters only. These LED strips generally include a conductive strip (e.g. copper) laminated with urethane and affixed to a flexible polyamide dielectric material such as Kapton having a pressure sensitive adhesive disposed on one side to form a flexible circuit board. The urethane forms a dome on the top of the strip to protect the circuit and helps support the emitters or needles. LEDs from the strip may be removed and replaced with emitters (e.g. stainless steel needles). The emitters may be pressed into the strip between LEDs or in place of LEDs and secured by various techniques, such as epoxy. The LEDs may be controlled by the microprocessor or by a separate controller. The LED strip in one ion generator may be single color LEDs, but a separate ion generator may use RGB multicolor LEDs so that the perceived color from the strip can be adjusted to a myriad of colors.

A high voltage low current source can be connected to one end of the strip with a suitable electrical connector. Ideally, the high voltage source is AC such that only a single row of connected discharge points is required. DC would require two rows of discharge points, one positive and one negative to create bipolar ionization. Alternately, a DC high voltage source could be connected to the single row of discharge point to create positive or negative ions only, not both. In one ion generator, the reference ground and emitter (high voltage output) is connected to the LED light strip or separately manufactured strip with emitters only. The high voltage AC output provides power to the emitters attached to the strip as well as the LEDs. The LEDs may be powered separately through a separate conductive pathway on the substrate.

The strips as described above may be mounted and used to sanitize, for example, a faucet, door handle, VFV/VRF (variable refrigerant flow/variable refrigerant volume) heating, ventilation, and air conditioning systems, traditional heating, ventilation, and air conditioning systems. Furthermore, it could be used for under cabinet lighting with a counter sanitizer, refrigerator lighting and sanitizing, sanitizing and lighting a bread box, or toy box. The flexible nature of the strips allow them to be installed any area that needs sanitizing and/or lighting. The flexible discharge points described in this invention are flexible and very small. The strips can be cut to any length with simple scissors for each installation in any application.

As illustrated in FIG. 13 the present invention is directed to a new ion electrode assembly. In developing this ion electrode assembly, a new ion generator was also developed that surprising does not have a ground electrode close in proximity to the ion electrode. More specifically, the ion generator uses an earth ground, or a ground from the surrounding environment, machine, apparatus, or device. This new configuration surprisingly generates for more effective or useable ions for sanitizing than the devices where the ground electrode is in close proximity to the ion electrode. It has been widely known that the closer the ground electrode and ion electrode are placed in proximity, the stronger the electrical field, and therefore, the more ions that are generated. However, it has been surprisingly found that when measured some distance away from the device, where the useable ions would occur that would perform the sanitizing, the number of useable ions is much greater, even given that a much weaker electrical field is generated when the ground electrode is in the surrounding environment and not in close proximity with a specific electrode. This increase in ions is exactly opposite the teaching currently in the art.

Figure 24:
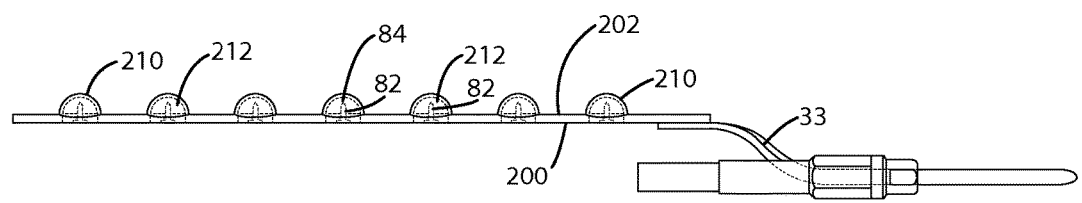
FIG. 24 is a side view of a new ion electrode assembly in FIG. 13 that is flexible.
Figure 25:
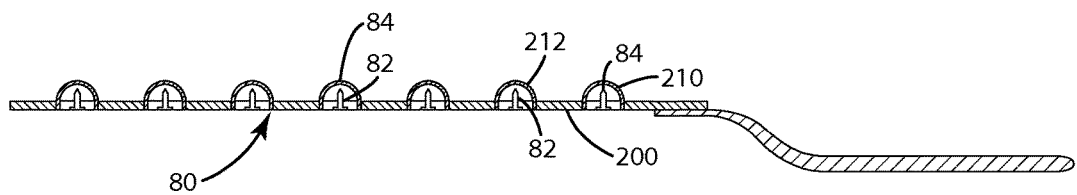
FIG. 25 is a sectional view of the new ion electrode assembly taken along lines A-A in FIG. 13.
Figure 26:
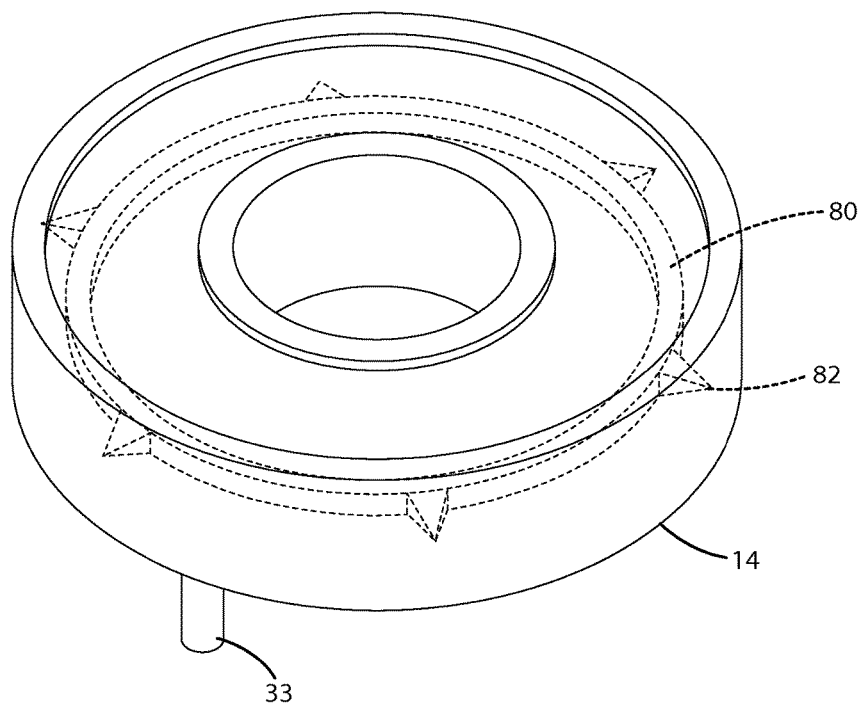
FIG. 26 is a top perspective view of an exemplary ion source assembly, with a concealed ion electrode and a substantially smooth exterior surface and no external groove for receiving the ion electrode.
Figure 30:
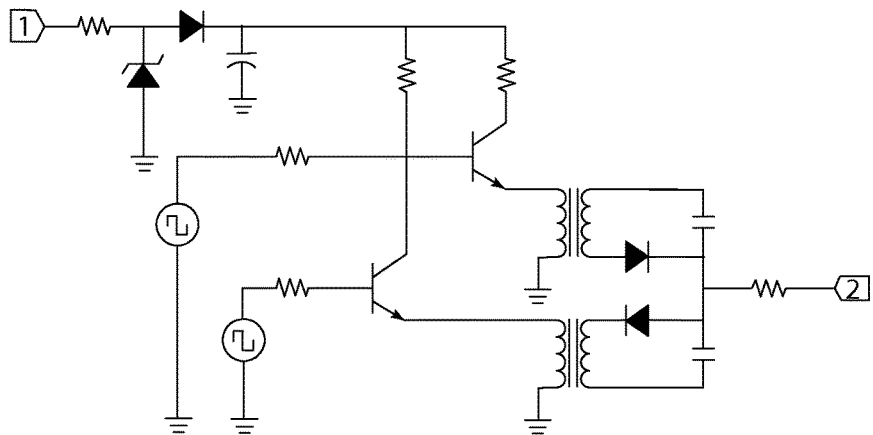
FIG. 30 is a schematic diagram of the ion generator using two flyback transformers.
Figure 31:
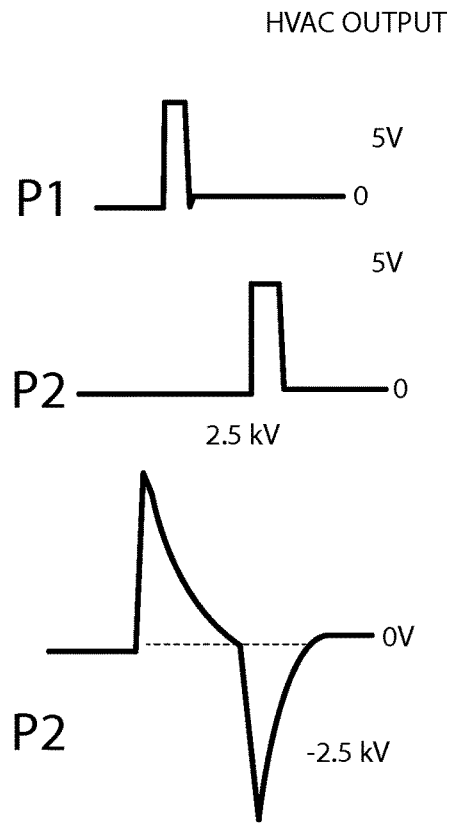
FIG. 31 is illustrates and exemplary input of P1 and P2 to the flyback transformers and the output on the ion electrode.
Figure 32:
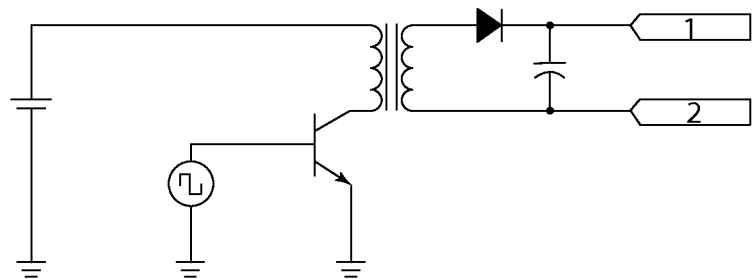
FIG. 32 is illustrates a schematic diagram of a flyback transformer used to create high voltage DC for bipolar ionization.
Figure 33:
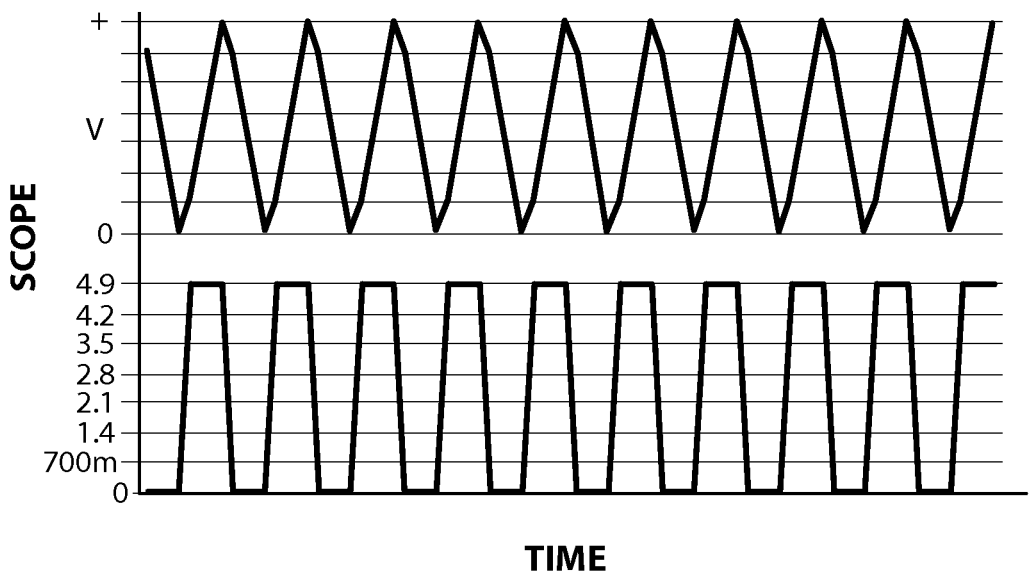
FIG. 33 is an exemplary output of the flyback converter in FIG. 32.

In addition, the present inventor has also surprisingly found that the ion sources may be covered by a dome of thin wall of dielectric material such as plastic or glass, thereby preventing injury for contact with the points. Even though the ion generator runs at a voltage that is not harmful to touch, enclosing the ion sources and connective surfaces prevents any shorting of the ion electrode assembly in a wide range of environments, including those that experience moisture. Surprisingly the domes still allow a generous amount of ions to pass through and in reality the ion electrode assembly disclosed herein provides sufficient ions in a compact package that substantially outperforms prior art devices with exposed electrode. The domes in FIGS. 13 and 24-25 are formed from a nonconductive material. In the present invention, the nonconductive material of the domes and cover has surprisingly been found to provide more useable ions at the location where the ions are desired, such as at a surface, hands, in the air in an HVAC system, over a coil in an HVAC system and the like. Placed in an HVAC system, such as before the filter, could prevent the filter from growing pathogens and other undesirable organisms, likewise placed proximate to the coil in and HVAC system that regularly experiences moisture, the present invention also prevents the growth of harmful pathogens and organisms which then can be spread by the HVAC system. It is well known that cool damp areas in HVAC systems can have harmful effect on people breathing the air from such HVAC systems. In addition, for ductless mini-split systems, there is very limited ability to filter the air, and typically no ability to put in an efficient free flowing filter that is capable of filtering out most pathogens. As stated above, the filters need to be frequently cleaned or changed, such as every two weeks on most systems and most users do not follow this schedule, which allows pathogens and unwanted organisms to grow on the filters. In view of the filtration limits with ductless min-split systems, so it is even more important to keep the coil free from harmful organisms and pathogens.

As illustrated in FIGS. 13, 24 and 25, the substrate is formed from a flexible material, such as an LED light strip, which allows reduction in shipping costs, as the material may be rolled, instead of being extended as required to ship rigid bars. The substrate generally includes a base material and a flexible conductive material applied thereto. The ion sources are in contact with the flexible conductive material. A substrate material this is nonconductive may be placed over the substrate and it and the domes may be injection molded. Of course, the ion electrode assembly could be formed without the substrate cover, the domes, or both. The ion electrode also includes a connector. Of course, modifications may be made to the ion electrode assembly as to size, shape, configuration.

FIGS. 24 and 25 represent an ion electrode assembly with a complete cover. While this will have greater length in shipping, the non-conductive cover provides the same function as the domes. The substrate 200 may be formed from a flexible material, or may be formed from a ridged material, to which the ion sources are attached. The substrate may be a metal plate with attached ion sources, such as through welding. As illustrated in FIGS. 24 and 25, the substrate 200 may be a flexible conductive material, with a flexible insulated layer or substrate cover 202 applied thereto. The cover is placed over the substrate and a fastener, such as the illustrated connectors and fasteners may be used. In some instances, the ion electrode 80 will include domes 210 over the ion sources 82 to form an air gap 212. It has been found that if the ion sources 82 are completely encased, over time they tend to break down the substrate cover and become exposed to the environment. It has been surprisingly been found, that even through the ion sources are not exposed to the air in which the ions are to be created, even though they are covered with a cover, such as the illustrated domes 210, the system still produces a wide range of ions, up to at least 6 feet away. Furthermore, the air gap to the dome 210 prevents the ion sources from breaking down the substrate cover 210 or domes. This electrode is particularly useful in the duct work of an HVAC system, although the connector and fasteners need to be insulated from and not contact any metal ducts.

It should be noted that the covers and domes are only capable of being used with the ion generator of the present invention having AC source applied to the ion sources. The AC system with the ion electrode assembly creates a field that extends above and through the nonconductive domes and covers, creating the ions in the air around the domes and covers. One big benefit of this surprising revelation that sufficient ions are generated from ion sources that are covered and not exposed to the environment is that it eliminates the need to clean the ion sources. In prior embodiments, the ion sources would collect dust and debris that would substantially reduce their efficiency and require cleaning. Cleaning of the needles can cause injury from the sharp points, so the use of domes and covers that surprisingly do not reduce the efficiency of the ion fields is a major step forward in creating a maintenance free ion electrode assembly. While the ion sources may be covered with a solid dielectric material, it has been found that eventually the ion sources will burn a hole through the solid material, which opens them to the environment and opens them to moisture and dust which can reduce the efficiency. As such, the dome or cover has been developed, which creates and air gap, but surprisingly provides as good of an ion field outside of the cover or dome. The air gap prevents the burning of holes through the cover or domes, creating a seal over the ion sources that protect them from moisture and dust, therefore making them maintenance free and maintaining their effectiveness even in dirty environments. It has also been found that the dome or cover causes the ions to be distributed over a wider area, causing a more effective ion field, with all the benefits listed above and creating a shock resistant barrier between the environment and the ion sources.

Figure 42:
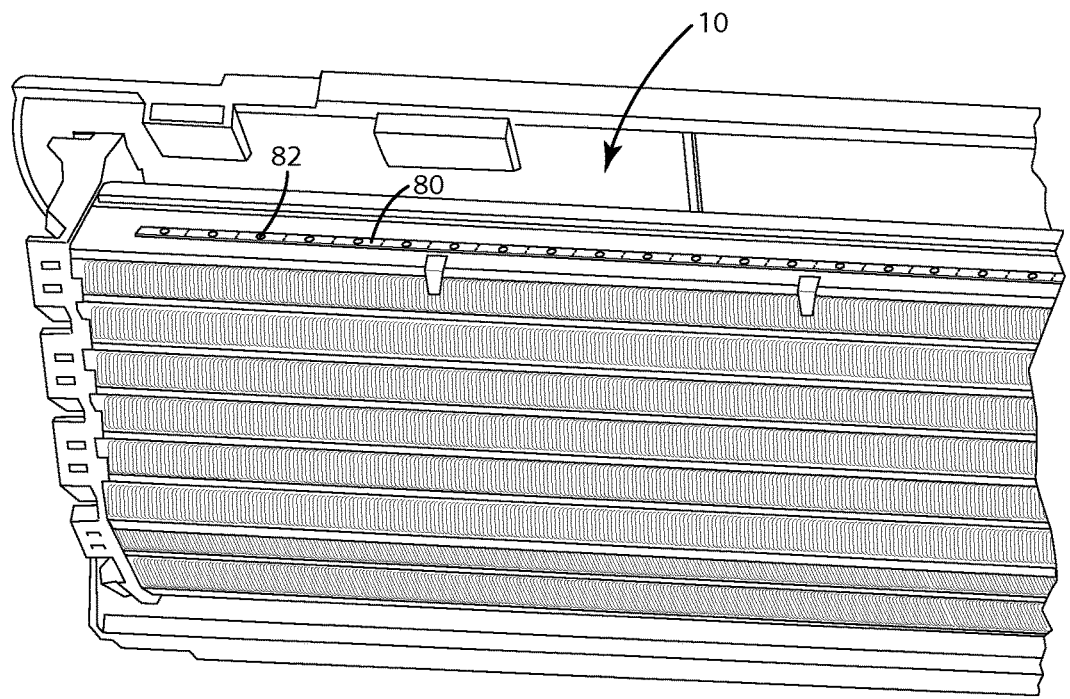
FIG. 42 is a photograph of a portion of a ductless mini-split HVAC system, including an ion electrode coupled to an area proximate to the air outlet to form the ion source assembly.
Figure 43:
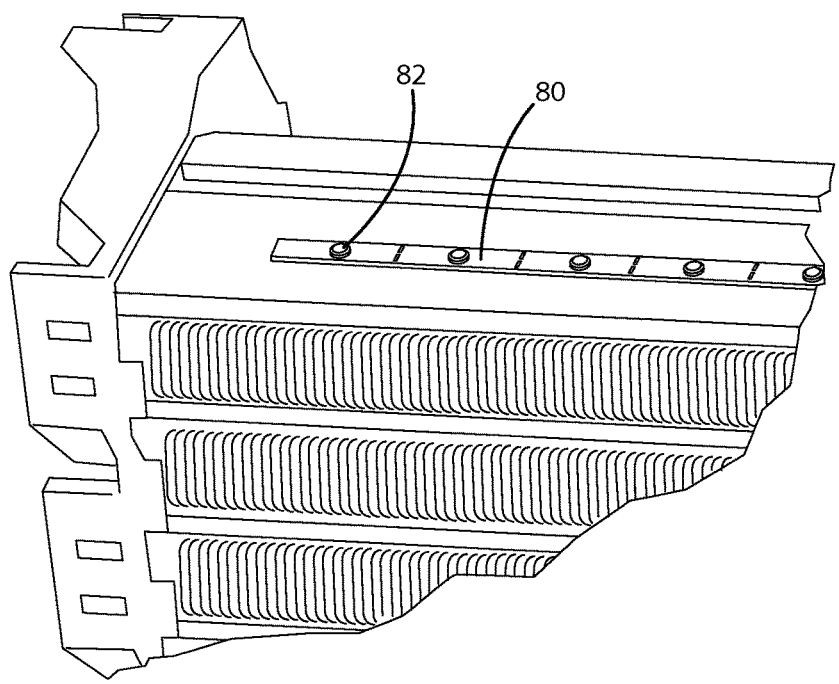
FIG. 43 is a photograph of an enlarged portion of the ductless mini-split HVAC system in FIG. 42, clearly showing the ion sources and the covers over the ion sources.

As illustrated in FIGS. 42 and 43, the fixture may be an appliance, such as a ductless mini-split HVAC system, where the ions clean and sanitize the appliance, and in turn the air emanating therefrom. The system of the present invention with the remote ion generation system 61 allows the controller 64 and ion generator 60 to be located within and control box of the ductless mini-split HVAC system, and the ion source assembly 61 to be located where needed, including the illustrated flexible ion electrode 80 with ion sources 82.

Obviously, many modifications and variations of the present invention are possible in light of the above teachings and may be practiced otherwise than as specifically described while within the scope of the appended claims. These antecedent recitations should be interpreted to cover any combination in which the inventive novelty exercises its utility. The use of the word "said" in the apparatus claims refers to an antecedent that is a positive recitation meant to be included in the coverage of the claims whereas the word "the" precedes a word not meant to be included in the coverage of the claims. In addition, the reference numerals in the claims are merely for convenience and are not to be read in any way as limiting.

The invention claimed is:

1. A sanitizer for generating ions in air, said sanitizer comprising:
   an ion source assembly comprising a base and an ion electrode situated within said base, said ion electrode including at least one ion source covered with a cover configured to isolate the ion sources from the air in which the ions are created; and
   an ion generator assembly comprising a controller within a housing and wherein said controller is in electrical communication with said ion electrode through a cable.

2. The sanitizer of claim 1 wherein said ion generator assembly includes a ground electrode.

3. The sanitizer of claim 1 wherein said controller is in communication with an external power supply and wherein said controller is in communication with a ground reference in said external power supply and wherein said controller is configured to use said ground reference in said external power supply as a ground electrode.

4. The sanitizer of claim 1 wherein said controller alternates the charge on said ion electrode.

5. The sanitizer of claim 1 wherein said base has an external surface and wherein said ion electrode is behind said external surface, and covered with a nonconductive cover.

6. The sanitizer of claim 5 wherein said ion electrode is located in an internal cavity on said base formed by said base and said cover and wherein said cavity is not exposed to the air in which the ions are created, and wherein an air gap surrounds said ion sources.

7. The sanitizer of claim 1 wherein said ion electrode is situated within a groove on said base, and wherein said base includes an external surface and an ion point on said ion source does not extend out of said groove, past said external surface, and wherein the ion sources are sealed from exposure to the air in which the ions are created.

8. The sanitizer of claim 1 wherein said controller is in electrical communication with a fixture proximate to said ion source assembly and wherein said fixture is configured to act as a ground electrode.

9. The sanitizer of claim 1 wherein said ion electrode produces a non-thermal plasma field and wherein said base is situated proximate to a faucet, and wherein said non-thermal plasma field is tuned such that any water exiting the faucet must pass through said plasma field and wherein said water passing through said non-thermal plasma field produces ions in the water, and wherein the ion sources are free from contact with the water.

10. The sanitizer of claim 1 wherein said ion electrode is formed from a flexible material with said ion sources protruding therefrom.

11. The sanitizer of claim 1 further including a battery in electrical communication with said controller.

12. The sanitizer of claim 11 further including a ground electrode extending from said controller.

13. The sanitizer of claim 1 wherein said ion source assembly and said ion generator assembly are located at least twelve inches apart.

14. The sanitizer of claim 10 wherein said ion electrode is formed from LED tape and includes both LEDs and ion sources.

15. The sanitizer of claim 10 wherein said flexible material includes a conductive metal tape and a strip substrate over said conductive metal tape, and said ion sources are spaced apart from one another.

16. The sanitizer of claim 15 wherein said flexible material includes ion source covers that are configured to not touch said ion sources and create an air gap around the ion sources and further prevent access to said ion sources, and sealing the ion sources from the air in which the ions are created.

17. A fixture sanitizer for sanitizing fixtures, appliances, hardware and surfaces, said fixture sanitizer comprising:
   an ion source assembly comprising a base and an ion electrode situated within said base, said ion electrode including at least one ion source includes an exterior surface and wherein said cavity is sealed from said external surface; and
   an ion generator assembly comprising a controller configured to provide an AC output to said ion electrode and wherein said controller is in electrical communication with said ion electrode and wherein said ion generator assembly is configured to receive electrical power from an external power supply having a reference ground and wherein said controller is configured to use the reference ground as a ground electrode.

18. The fixture sanitizer of claim 17 wherein said ion electrode is situated within a cavity created by a cover.

19. The fixture sanitizer of claim 18 wherein base includes an exterior surface, and wherein said cavity is sealed from said external surface within said cover.

20. The fixture sanitizer of claim 19 wherein said base includes an inner surface and wherein said passage extends between said inner surface and said cavity.

21. The sanitizer of claim 17 wherein said cover is a dome.

22. The sanitizer of claim 21 wherein said dome is sealed.

23. The sanitizer of claim 19 wherein said cover is a dome.

24. A fixture sanitizer comprising:
   an ion source assembly having an ion electrode including at least one ion source and wherein said ion electrode is formed from a flexible substrate to which said at least one ion source is coupled and a sealed substrate cover configured to create an air gap around said ion source; and
   an ion generator assembly comprising a controller configured to provide an AC output to said ion electrode and wherein said controller is in electrical communication with said ion electrode and wherein said ion generator assembly is configured to receive electrical power from an external power supply having a reference ground and wherein said controller is configured to use the reference ground as a ground electrode.

25. The sanitizer of claim 24 wherein said substrate cover seals said ion source from the surrounding environment, yet said air gap prevents said ion source from touching said substrate cover proximate to a point on said ion source.

26. A sanitizer comprising:
   a flexible ion source assembly comprising a base and an ion electrode formed from a flexible LED tape situated within said base, said ion electrode including at least one ion source protruding therefrom and LEDs; and
   an ion generator assembly comprising a controller within a housing and wherein said controller is in electrical communication with said ion electrode through a cable.

* * * * *